US012579648B2

(12) United States Patent
Shinagawa et al.

(10) Patent No.: US 12,579,648 B2
(45) Date of Patent: Mar. 17, 2026

(54) METHODS AND SYSTEMS FOR IDENTIFYING SLICES IN MEDICAL IMAGE DATA SETS

(71) Applicant: Siemens Healthineers AG, Forchheim (DE)

(72) Inventors: Yoshihisa Shinagawa, Downingtown, PA (US); Halid Yerebakan, Carmel, IN (US); Gerardo Hermosillo Valadez, West Chester, PA (US); Mahesh Ranganath, Malvern, PA (US); Simon Allen-Raffl, West Chester, PA (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 597 days.

(21) Appl. No.: 17/850,796

(22) Filed: Jun. 27, 2022

(65) Prior Publication Data

US 2022/0414883 A1 Dec. 29, 2022

(30) Foreign Application Priority Data

Jun. 29, 2021 (EP) .................................... 21182340

(51) Int. Cl.
*G06T 7/00* (2017.01)
*G16H 30/40* (2018.01)

(52) U.S. Cl.
CPC ........... *G06T 7/0014* (2013.01); *G16H 30/40* (2018.01); *G06T 2207/20081* (2013.01); *G06T 2207/20108* (2013.01); *G06T 2207/30004* (2013.01)

(58) Field of Classification Search
CPC ......... G06T 7/0014; G06T 2207/20081; G06T 2207/20108; G06T 2207/30004;
(Continued)

(56) References Cited

U.S. PATENT DOCUMENTS

| | | | | |
|---|---|---|---|---|
| 2011/0075901 A1* | 3/2011 | Nakamura | ............. | G16H 30/40 |
| | | | | 382/128 |
| 2015/0279061 A1* | 10/2015 | Kutsuna | ................ | G06T 7/0012 |
| | | | | 382/131 |

(Continued)

FOREIGN PATENT DOCUMENTS

| | | | | |
|---|---|---|---|---|
| CN | 109102532 A | | 12/2018 | |
| CN | 110889005 A | | 3/2020 | |
| JP | 2001137230 A | * | 5/2001 | |
| WO | WO-2021061710 A1 | * | 4/2021 | ......... G01R 33/5608 |

OTHER PUBLICATIONS

Xiao, Gaoyu, et al. "Determining histology-MRI slice correspondences for defining MRI-based disease signatures of prostate cancer." Computerized Medical Imaging and Graphics 35.7-8 (2011): 568-578. (Year: 2011).*

(Continued)

*Primary Examiner* — Molly Wilburn
(74) *Attorney, Agent, or Firm* — Harness, Dickey & Pierce, P.L.C.

(57) ABSTRACT

Computer-implemented methods and systems for identifying corresponding slices in medical image data sets are provided. For example, the systems and methods are based on identifying corresponding slices by systematically quantifying image similarities between the slices comprised in one medical image data set and the slices comprised in another medical image data set.

15 Claims, 6 Drawing Sheets

(58) Field of Classification Search
CPC ............. G06T 7/38; G06T 2207/10072; G06T 2207/20084; G06T 7/0012; G06T 2207/10081; G06T 2207/10116; G16H 30/40; G16H 50/20; G06F 18/22; G06F 18/2413; G06V 2201/03; G06V 10/443; G06V 10/761; G06V 10/82; G06N 3/084
See application file for complete search history.

(56) References Cited

U.S. PATENT DOCUMENTS

| | | |
|---|---|---|
| 2018/0360313 A1 | 12/2018 | Zhang |
| 2019/0030371 A1* | 1/2019 | Han ..................... A61N 5/1039 |
| 2020/0058390 A1 | 2/2020 | Kohle et al. |
| 2021/0133976 A1* | 5/2021 | Carmi ................... G16H 30/20 |
| 2021/0166406 A1 | 6/2021 | Sperl et al. |

OTHER PUBLICATIONS

Yu, Peicong, Chueh Loo Poh, and Kenneth Sheah. "Automatic Identification of Corresponding CT Images Having the Same Lymph Node in Longitudinal Studies." 2010 4th International Conference on Bioinformatics and Biomedical Engineering. IEEE, 2010. (Year : 2010).*

Cheng, Xi: "Deep similarity learning for multimodal medical images"; Computer Methods in Biomechanics and Biomedical Engineering: Imaging & Visualization; Apr. 6, 2016 (Apr. 6, 2016), pp. 1-5, XP055414487; 2015.

De Vos Bob D. et al: "Automatie Slice Identification in 3D Medical Images with a ConvNet Regressor"; Deep Learning and Data Labeling for Medical Applications; Oct. 21, 2016 (Oct. 21, 2016), pp. 161-169, XP055868757.

* cited by examiner

METHODS AND SYSTEMS FOR IDENTIFYING SLICES IN MEDICAL IMAGE DATA SETS

CROSS-REFERENCE TO RELATED APPLICATION(S)

The present application hereby claims priority under 35 U.S.C. § 119 to European patent application number 21182340.6 filed Jun. 29, 2021, the entire contents of which are hereby incorporated herein by reference.

FIELD

The technical field of the application is methods and systems for identifying one or more slices in medical image data sets. In particular, the application relates to identifying corresponding slices in different medical image series. Further, the application relates to identifying those slices of a medical image series that correspond to a key image associated to that image series.

TECHNICAL BACKGROUND

A medical image study may include a series of parallel image slices spanning an anatomic region of a patient. The thickness of the slices varies with the imaging modality and is typically 1-5 mm. In order to review a medical image study, a physician may use a scroll bar or the like to step from image to image. When reading a medical image study, the physician may make annotations on various images and include details in the annotations such as lesion measurements. A patient with multiple lesions typically has each lesion annotated, which can be spatially spread over a volume with many non-annotated image slices in between. Upon compiling a medical report based on his review of the medical image study, the physician typically selects a few images and indicates the selected images as key images which may be directly included in the report or separately archived.

Over time, a patient can have many studies. In the clinical routine, the physician compares images from the various studies to analyze a change in lesions and other tissues. To do so, the physician typically has the current study open on one monitor or in one window and opens a second or prior study on another monitor or window to compare.

SUMMARY

After finding a comparable study, the physician selects an image in the current study and/or a key image in a prior study, and to find a comparable image, the physician typically must scroll through images in the other study which consumes valuable clinical time. This is even more so, as each study contains a plurality of slices from several hundred to several thousand images or slices. For the same reason, as the physician rapidly moves through the images, relevant slices may flash by so quickly that they are easily missed. Moreover, of spending time performing this navigation often means that there is less time for comparing the images. Because of that, meaningful relationships may be overlooked.

Example embodiments provide methods and systems capable of providing improved ways to identify slices in medical image studies. In particular, example embodiments provide methods and systems which enable the identification of slices in image studies which correspond to key images or to slices in other image studies related to the image study at hand.

According to at least one example embodiment, a computer-implemented method includes receiving a first medical image data set; receiving a second medical image data set, the second medical image data set being different from the first medical image data set; and identifying, from a plurality of slices comprised in the second medical image data set, at least one corresponding slice based on degrees of similarity between image data comprised in the first medical image data set and individual slices of the second medical image data set.

According to at least one example embodiment, the first medical image data set comprises a plurality of slices, and the identifying includes identifying for each of a plurality of slices of the first medical image data set one corresponding slice of the second medical image data set to determine a slice correspondence between the first medical image data set and the second medical image data set, the degrees of similarity being respectively based on a similarity between an individual slice of the first medical image data set and an individual slice of the second medical image data set.

According to at least one example embodiment, the method further includes determining an anatomical overlap between an image volume of the first medical image data set and an image volume of the second medical image data set based on the identified slice correspondence; evaluating a degree of comparability of the second medical image data set with the first medical image data set based on the determined anatomical overlap; and providing the degree of comparability to a user via a user interface.

According to at least one example embodiment, the method further includes receiving an input from a user indicative of a selection of a slice of the first medical image data set to designate a selected slice; identifying, from the plurality of slices of the second medical image data set, the slice corresponding to the selected slice based on the identified slice correspondence; and providing the slice corresponding to the selected slice.

According to at least one example embodiment, the method further includes extracting at least one image descriptor from image data of the first medical image data set; and respectively extracting a corresponding image descriptor from each of a plurality of slices of the second medical image data set, wherein the degrees of similarity are respectively based on a comparison between the extracted at least one image descriptor of the first medical image data set and the corresponding image description of the second medical image data set.

According to at least one example embodiment, the first medical image data set comprises a plurality of slices and the method further comprises extracting an image descriptor from each of a plurality of slices of the first medical image data set.

According to at least one example embodiment, the first medical image data set is associated with a first medical imaging modality, the second medical image data set is associated with a second medical imaging modality, and the first medical imaging modality is based on an imaging technology different from an imaging technology of the second modality, the first modality being based on an x-ray imaging technology and the second medical image data set being based on a magnetic resonance imaging technology.

According to at least one example embodiment, the first medical image data set comprises a two-dimensional key image indicative of at least one finding previously reported for a patient; and the second medical image data set comprises an image study the reference image has been extracted from upon reporting the at least one finding for the patient.

According to at least one example embodiment, the method further includes resampling the second medical data set based on the first medical image data set in order to define a plurality of slices in the second medical image data set.

According to at least one example embodiment, the identifying the at least one corresponding slice includes applying a trained function on the first and second medical image data sets, wherein the trained function is configured to determine degrees of similarities between two-dimensional medical images; and the trained function applies a learned metric to determine degrees of similarity between two-dimensional medical images, the trained function including a deep metric learning network.

According to at least one example embodiment, the trained function is configured to determine degrees of similarities between two-dimensional medical images by comparing a first candidate image to a reference image and comparing a second candidate image to the reference image, the reference image being extracted from one of the first and second medical image data sets and the first and second candidate images being extracted from the respective other one of the first and second medical image data set; and determining which one of the first and second candidate images has a higher degree of similarity to the reference image.

According to at least one example embodiment, a computer-implemented method includes receiving a two-dimensional key image, the two-dimensional key image indicative of at least one finding previously reported for a patient; retrieving a first medical image data set corresponding to the key image; identifying, from a plurality of slices of the first medical image data set, at least one corresponding slice of the first medical image data set with respect to the key image, the identifying being based on degrees of similarity between the key image and individual slices of the first medical image data set to provide a first assignment between the key image and the at least one corresponding slice of the first medical image data set; receiving a second medical image data set, the second medical image data set at least partially depicting a same body part of the patient as the first medical image data set, the second medical image data set having been acquired at a different point in time than the first medical image data set; identifying, for each of the plurality of slices of the first medical image data set one corresponding slice of a plurality of slices of the second medical image data set, the degrees of similarity being respectively based on a similarity between an individual slice of the first medical image data set and an individual slice of the second medical image data set to provide a second assignment between slices of the first medical image data set and slices of the second medical image data set; and selecting at least one slice from the second medical image data set based on the first assignment and on the second assignment to provide a selected slice, the selected slice having a degree of similarity to the key image.

According to at least one example embodiment, a system includes an interface configured to receive a first medical image data set and a second medical image data set, the second medical image data set being different from the first medical image data set; and a computing unit configured to cause the system to identify, from a plurality of slices comprised in the second medical image data set, at least one corresponding slice based on degrees of similarity between image data comprised in the first medical image data set and individual slices of the second medical image data set.

According to at least one example embodiment, the first medical image data set comprises a plurality of slices, and the computing unit is configured to cause the system to identify for each of a plurality of slices of the first medical image data set one corresponding slice of the second medical image data set to determine a slice correspondence between the first medical image data set and the second medical image data set, the degrees of similarity being respectively based on a similarity between an individual slice of the first medical image data set and an individual slice of the second medical image data set.

According to at least one example embodiment, the computing unit is configured to cause the system to determine an anatomical overlap between an image volume of the first medical image data set and an image volume of the second medical image data set based on the identified slice correspondence; evaluate a degree of comparability of the second medical image data set with the first medical image data set based on the determined anatomical overlap; and provide the degree of comparability to a user via a user interface.

According to at least one example embodiment, the computing unit is configured to cause the system to receive an input from a user indicative of a selection of a slice of the first medical image data set to designate a selected slice; identify, from the plurality of slices of the second medical image data set, the slice corresponding to the selected slice based on the identified slice correspondence; and provide the slice corresponding to the selected slice.

According to at least one example embodiment, the computing unit is configured to cause the system to extract at least one image descriptor from image data of the first medical image data set; and respectively extract a corresponding image descriptor from each of a plurality of slices of the second medical image data set, wherein the degrees of similarity are respectively based on a comparison between the extracted at least one image descriptor of the first medical image data set and the corresponding image description of the second medical image data set.

According to at least one example embodiment, the first medical image data set comprises a plurality of slices and the computing unit is configured to cause the system to extract an image descriptor from each of a plurality of slices of the first medical image data set.

According to at least one example embodiment, a computer program product comprising program elements when executed by a computing unit, cause the computing unit to perform a method according to at least one example embodiment.

According to at least one example embodiment, a non-transitory computer-readable medium comprising program elements, when executed by a computing unit, are configured to cause a method according to at least one example embodiment to be performed.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the present invention on the contained embodiments. Same components or parts can be labeled with the same reference signs in different figures. In general, the figures are not drawn to scale. In the following.

DETAILED DESCRIPTION

Figure 1:
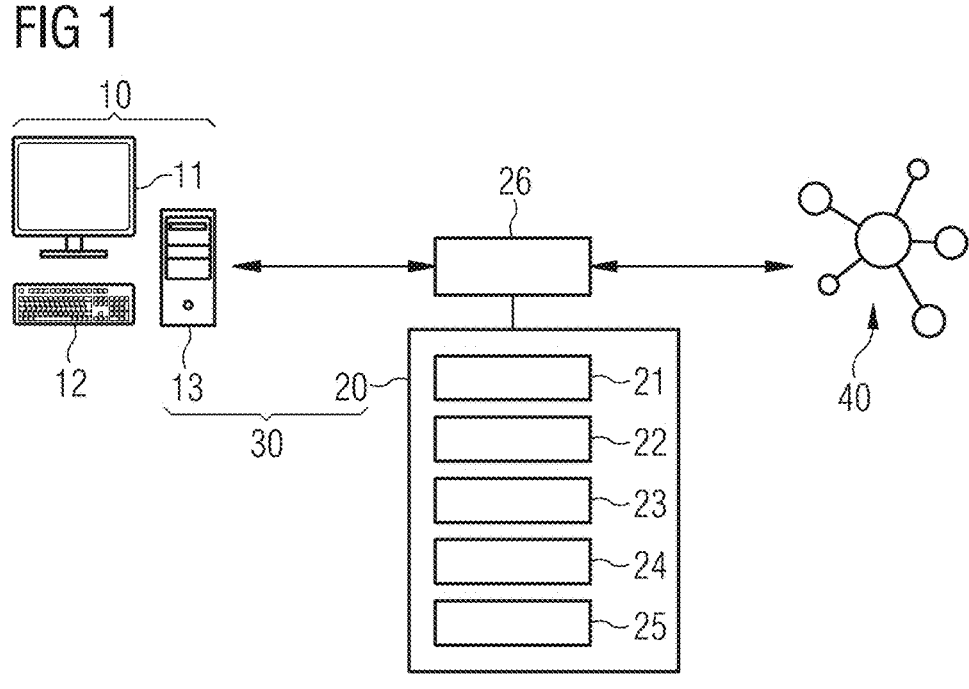
FIG. 1 depicts a system for carrying out methods based on an identification of corresponding slices in medical image data sets according to an embodiment.

Example embodiments provide methods for identifying one or more slices in a medical image data set, corresponding systems, a corresponding method for providing a trained function, corresponding computer-program products and computer-readable storage media according to one or more of the independent claims. Alternative and/or preferred embodiments are subject of the dependent claims.

In the following, the technical solution according to example embodiments of the present invention is described with respect to the claimed apparatuses as well as with respect to the claimed methods. Features, advantages or alternative embodiments described herein can likewise be assigned to other claimed objects and vice versa. In other words, claims addressing the inventive methods can be improved by features described or claimed with respect to the apparatuses. In this case, e.g., functional features of the methods are embodied by objective units, modules, or elements of the apparatus.

The technical solution will be described both with regard to methods and systems for identifying one or more slices in medical image data sets and also with regard to methods and systems for providing trained functions. Features and alternate forms of embodiment of data structures and/or functions for methods and systems for identification can be transferred to analogous data structures and/or functions for methods and systems for providing trained functions. Analogous data structures can, in particular, be identified by using the prefix "training". Furthermore, the trained functions used in methods and system for identifying one or more slices in medical image data sets can, in particular, have been adjusted and/or trained and/or provided by methods and systems for adjustment of trained functions.

According to one aspect, a computer-implemented method for identifying one or more slices in a medical image data set is provided. The method comprises a plurality of steps. A first step is directed to receiving a first medical image data set. Another step is directed to receiving a second medical image data set different from the first medical image data set. A further step is directed to identifying, from a plurality of slices comprised in the second medical image data set, at least one corresponding slice with respect to the first medical image data set based on degrees of similarity between the image data comprised in the first medical image data set and individual slices of the second medical image data set.

First and second medical image data sets may respectively relate to a medical image study. Such medical image studies may relate to three-dimensional data sets providing three dimensions in space. First and second medical image data sets may respectively depict a body part of a patient in the sense that they contain three-dimensional image data of the patient's body part. Medical image studies may, for example, be in the form of an array of voxels. Such arrays of voxels may be representative of intensity, absorption or other parameters as a function of three-dimensional position, and may, for example, be obtained by suitable processing of measurement signals obtained by a medical imaging modality. A medical imaging modality corresponds to a system used to generate or produce medical images. For example, a medical imaging modality may be a computed tomography system (CT system), a magnetic resonance system (MR system), an angiography (or C-arm X-ray) system, a positron-emission tomography system (PET system) or the like. Specifically, computed tomography is a widely used imaging method and makes use of "hard" X-rays produced and detected by a specially rotating instrument. The resulting attenuation data (also referred to as raw data) is presented by a computed analytic software producing detailed images of the internal structure of the patient's body parts. The produced sets of images are called CT-scans which may constitute multiple series of sequential images to present internal anatomical structures in cross sections perpendicular to the axis of the human body. Magnetic Resonance Imaging (MRI), to provide another example, is an advanced medical imaging technique which makes use of the effect magnetic field impacts on movements of protons. In MRI machines, the detectors are antennas and the signals are analyzed by a computer creating detailed images of the internal structures in any section of the human body. Accordingly, the depicted body part of the patient in general will comprise a plurality of anatomies and/or organs. Taking a chest image as an example, first and second medica image data sets may show lung tissue, the rib cage, lymph nodes and others.

Each medical image data set or image study may comprise a plurality of (predefined) images or image slices. However, the medical image data sets may as well relate to an isotropic or isometric image volume lacking defined cross-sectional or sequential images where slices or individual images may be arbitrarily defined.

Further, the first medical image data set may also relate to an individual image and, in particular, to a so-called key image representative of a particular finding or pathology of the patient.

The medical image data sets may be stored in a standard image format such as the Digital Imaging and Communications in Medicine (DICOM) format and in a memory or computer storage system such as a Picture Archiving and Communication System (PACS), a Radiology Information System (RIS), and the like. "Receiving" may mean that first and second medical image data sets are directly received from the medical imaging modalities. Further "receiving" may mean that first and second medical image data set are retrieved from an appropriate memory such as a picture archiving and communication system (PACS) or any other suitable medical image storing facility.

First and second medica image data sets may be different from one another in that they have been acquired at different points in time, show a different imaging volume, were acquired using different imaging modalities, and/or relate to different patients and so forth. In particular, the first medical image data set may relate to a subset of the second medical image data set. In particular, the first medical image data set may comprise one or more images/slices (previously) extracted from the second medical image data set, e.g., as key images.

Identifying one or more slices in the second medical image data set may mean determining, for each of the plurality of slices in the second medical image data set, a similarity metric representing a similarity between image data of the first medical image data set and the respective slice of the second medical image data set. Based on this evaluation, the slice or the slices having the greatest similarity with the image data of the first medical image data set may be selected and identified. For instance, all slices having a similarity above a predetermined threshold may be selected. Alternatively, the slice with the highest similarity may be selected. The result of determining a similarity metric between two images may be a degree of similarity between the images.

The arrangement of slices in the second medical image data set may be determined by the imaging modality or post-processing scheme used. If the second medical image data sets do not comprise any slices by default, slices may artificially be defined in the imaging volume spanned by the second medical image data set. Optionally, this may happen as a function of the image data comprised in the first medical image data set in order to optimally pre-process the second medical image data set for the ensuing comparison of the two image studies.

In other words, the method automatically identifies one or more slices in a medical image data set (here: the second medical image data set) which correspond to reference medical image data (here: the first medical image data set). This automatic retrieval of slices in a medical image data set is based on a quantification of the respective image similarity between the target (here: the second medical image data set) and the reference (here: the first medical image data set) image data. With that, a tool is provided capable of automatically retrieving those slices in image studies which are relevant in view of reference image data, e.g., in form of a prior study or one or more key images. Accordingly, a physician no longer has to scroll through the image studies by hand in order to track down relevant slices. Not only this brings about a considerable time saving, but also renders the process less error prone and improves reproducibility. The matching of slices in the different medical image studies is based on an evaluation of degrees of similarities between individual images. In comparison to other methods, this has the advantage of comparably fast processing times. Moreover, image similarities often still yield reasonable results in cases where other methods, e.g., methods based on image registrations or the detection of anatomic landmarks are not applicable. This may be the case if the variations between individual slices are so huge that no registration is possible or if no landmarks can be detected. Hence, it also becomes possible to readily synchronize very different image data sets, which may relate to different patients or which have been acquired using different imaging protocols or imaging modalities altogether.

According some examples, the first medical image data comprises at least a key image, wherein the one or more slices identified in the second medical image data set have a certain degree of similarity with the key image.

The key image may be comprised in a medical report. According to some examples, the first medical image data set may comprise a medical report. According to some examples, the method may further comprise extracting the key image from the medical report. The key image may be based on a slice comprised in the second medical image data set. The key image may comprise one or more annotations, which annotations may, for instance, have been made by a user or an automatic annotation tool. Annotations may include multi-media formats such as text, graphics, voice, etc. Annotations may relate to geometric objects, freehand drawings, measurement lines, text boxes, etc., overlaying the image slice, or separate from the associated image such as in the form of a sidebar, palate, icons, etc. The annotations including their size, location, orientation, etc. may be stored with the associated key image. Further, annotation may serve as bookmarks highlighting relevant slices. The annotations and associated key image may be stored as pieces of an object, package, etc., or separately and dynamically linked via a database or image meta-data. According to other examples, the key image may comprise a medical image not directly related to the second medical image data set. For instance, such key images may be images extracted from a different image study of the same patient or a different patient having a similar clinical condition. Further, key images may also be generic images representative of a certain diseases which may be, for instance, extracted from electronic compendia or guidelines.

Independent of the source of the key image, the method automatically retrieves those slices of the second medical data set having a high degree of similarity with the key image. According to some examples, only the slice with the greatest degree of similarity with the key image is identified. For instance, if the key image is based on a slice previously extracted from the second medical image data set, the method will then identify that slice in the second medical image data set the key image is based on. This enables the user to re-examine the original image data underlying the key image and also explore the neighboring slices.

According to some examples, the method further comprises automatically identifying one or more key images in the first medical image data set. For instance, the one or more key images may be identified by electronically searching the first medical image data set for annotations previously included therein. In particular, the one or more key images may be identified by electronically searching a plurality of slices comprised in the first medical image data set for annotations. According to other examples, the identification of one or more key images may include searching the first medical image data set (or a plurality of slices comprised in the first medical image data set) for one or more lesions, e.g., using appropriate computer-aided detection algorithms. Key images could then relate to those slices in which one or more lesions have been detected.

The automatic identification of one or more key images in the first medical image data set means that potentially relevant image information is automatically detected in the first medical image data set where it would be worthwhile to review the corresponding slices in the second medical image data set. In particular, this may be advantageous if the first medical image data set relates to a prior study of a patient and the second medical image data set relates to a follow-up image study of the patient.

According to some examples, the method may further comprise extracting an image descriptor from the at least one key image and extracting a corresponding image descriptor from each of a plurality of slices of the second medical image data set, with the degrees of similarity then respectively being based on a comparison, i.e., similarity, between the image descriptor and individual corresponding image descriptors.

In some examples, an image descriptor may be a vector representing or characterizing the underlying image data of either the key image or the slices of the second medical image data set. In some examples, the plurality of slices may represent a subset of the slices comprised in the second medica image data set. According to other examples, the plurality of slices may relate to all of the slices comprised in the second medical image data set. In some examples, the image descriptor may be determined by encoding the key image or the respective slices of the second medical image data set using a particular image descriptor encoding algorithm. Features of the key image or the respective slices, such as a visual manifestation of a medical abnormality, a pattern, an anatomy, a medical landmark and so forth as indicated by the key image or the respective slice may be encoded in the respective image descriptor. The image descriptors may be calculated on-line, e.g., upon the receipt of the first or second medical image data sets. Alternatively, image descriptors may be held available as-pre-generated data items stored in a database, e.g., alongside first and second medical data sets.

According to some examples, the degrees of similarity may be calculated by applying a similarity metric representing how similar the key image is to a slice of the second medical image data set. Another expression for similarity metric may be distance metric. In some examples, the similarity metric may be configured to quantify a distance in vector or feature space between the image descriptor of the key image and the image descriptor of a respective one of the slices of the second medical image data set. According to some examples predetermined mathematical functions may used to calculate such a distance such as the cosine similarity or the Euclidean distance and so forth. According to other examples, the similarity or distance metric may comprise a learned metric which has been derived by machine learning. According to some implementations, the extraction of the image descriptors and/or the evaluation of a similarity metric as whole may be performed by one or more trained functions (see below).

According to some examples, the first medical image data set comprises a plurality of (image) slices, and the step of identifying the at least one corresponding slice may then comprise identifying for each of a plurality of slices of the first medical image data set one corresponding slice of the second medical image data set, the degrees of similarity being respectively based on a similarity between an individual slice of the first medical image data set and an individual slice of the second medical image data set.

In other words, the method thus unambiguously matches slices in the first medical image data set with corresponding slices in the second medical image data set based on image similarity considerations. With that, the slices in the two different medical image studies are synchronized. Accordingly, when scrolling through the second medical image data set, the user can be automatically provided with the respectively corresponding slice of the first medical image data set and vice versa. Hence, the user is brought into a position to directly compare first and second medical image data sets side-by-side. According to some examples, the result of such a matching step may be provided in the form of data association that unambiguously assigns each of a plurality of slices of the first medical data set to a corresponding slice of plurality of slices of the second medical image data set.

In cases where the identification of corresponding slices is ambiguous, the method may make use of auxiliary conditions to pinpoint corresponding slices. Such auxiliary conditions may be the respective slice order in first and/or second medical image data sets and/or a measure of the overall similarity. Therefore, according to an aspect, the step of identifying, for each of a plurality of slices of the first medical image data set, one corresponding slice of the second medical image data set may additionally be based on the slice order in the first and/or second medical image data sets and/or may additionally be performed under the condition that (such that) the overall degree of similarity is maximized. In this regard, the overall degree of similarity may be the cumulative similarity (the sum of the individual degrees of similarity) between the corresponding slices of first and second medical image data sets as determined by the method. The slice order can be conceived as the natural sequence of slices as determined by the imaging process or simply the anatomy of the patient.

According to some examples, the method may further comprise the steps of extracting an image descriptor from each of a plurality of slices of the first medical image data set, and extracting a corresponding image descriptor from each of a plurality of slices of the second medical image data set, with the degrees of similarity being respectively based on a similarity between an individual image descriptor and an individual corresponding image descriptor. The image descriptors may essentially correspond to the ones previously described. In particular, degrees of similarity may likewise be calculated using the above-mentioned similarity metric.

According to some examples, the method may further comprise determining an anatomical overlap between the image volume of first medical image data set and the image volume of the respective second medical image data set based on the identified corresponding slices. On the basis of the determined anatomical overlap the method may then evaluate the suitability of the second medical image data set for comparative analysis in conjunction with the first medical image data set (i.e., a degree of comparability). The method may further comprise providing the determined suitability to a user via a user interface and/or selecting the second medical image data for comparative analysis based on the determined suitability.

According to some examples, the method may be used to systematically evaluate image studies according to their suitability for comparison with a target image study. Transferred to follow-up reading, where a user seeks to compare the current study to an appropriate prior study, this may enable to systematically evaluate available prior studies according to their comparability to the current study. In case of no or only limited anatomical overlap, the prior study is likely not suited for follow-up reading. The user may be notified accordingly and/or the study may be de-selected for further comparative analysis. By consequence, the user does no longer have to manually load and inspect image studies in order determine whether or not they are suited for comparative reading. This spares time and computational resources. A second medical image data set may, for instance, be selected for comparative reading if the degree of suitability is higher than a predetermined threshold. The degree of suitability may, for instance, be the anatomical overlap which, in turn, may be measured in the number of corresponding slices. In addition, the degree of suitability may include further factors such as the general comparability of two image studies, e.g., in terms of the imaging modalities used, or the time span between the first and second medical image studies have been taken.

According to some examples, the method may further comprise receiving an input from a user indicative of a selection of a slice of the first medical image data set in order to designate a selected slice, identifying, from the plurality of slices of the second medical image data set, the slice corresponding to the selected slice based on the step of identifying the corresponding slices (i.e., based on the identified association), and displaying/providing the slice corresponding to the selected slice.

The aforementioned user input may be received via a user interface and the displaying may be carried out using the same user interface. Such user input may generally be directed to a selection of a slice in a medical image study, e.g., by scrolling through the study. The identification of the corresponding slice may be repeated once a new user input is received. Thus, when scrolling through the first medical image study, the user is automatically provided with that slice of the second medical image which corresponds to the currently selected slice in the first medical image study. With that, the user may directly compare corresponding slices in order to assess whether a pathological condition of the patient has improved or got worse.

According to some examples, first and second medical image data sets may at least partially depict the same body part of a patient at different points in time. In other words, the first medical image data set may relate to a prior study and the second medical image data set may relate to a follow-up study or vice versa.

According to some examples, the method may comprise: identifying one or more reference slices in the first medical image data set, the one or more reference slice respectively comprising one or more prior lesions; identifying, in the second medical image data set the slices respectively corresponding to the identified reference slices based on the step of identifying for each of a plurality of slices of the first medical image data set one corresponding slice of the second medical image data set (or based on the aforementioned association); detecting, in the slices corresponding to the identified reference slices, one or more follow-up lesions; matching the prior lesions with the follow-up lesions; determining a temporal evolution of the detected prior lesions based on the matched follow-up lesions; and providing the temporal evolution.

With that, the user is automatically provided with an estimate how prior lesions progressed. According to some examples, the reference slices may be identified by automatically searching the slices comprised in the first medical image data set for prior lesions, e.g., by using a computer-aided detection algorithm. According to other examples, the reference slices may be identified by evaluating existing annotations comprised in the first medical image data set. Optionally, these may then be searched for prior lesions using a computer-aided detection algorithm (in particular, if the prior lesions are not identified by the existing annotations). Follow-up lesions may automatically be detected likewise using a computer-aided detection algorithm. Alternatively, lesions may be detected based on user inputs indicating one or more lesions in the respective slices. Matching prior and follow-up lesions may, e.g., be based on the step of identifying corresponding slices and the respective relative positions of prior and follow-up lesions in the respective slices. Determining a temporal evolution may comprise extracting at least a measured quantity form the prior and follow-up lesion, respectively, and compare the extracted measured quantities over time. The extracted quantities may, for instance, relate to the volume of a lesion, the dimensions of a lesion (such as the size, diameter, surface), an estimated degree of malignancy, and so forth.

According to some examples, the method may further comprise receiving at least a third medical image data set. The step of identifying the at least one corresponding slice may then comprise identifying for each of a plurality of slices of the first medical image data set one corresponding slice of the third medical image data set, the degrees of similarity being respectively based on a similarity between an individual slice of the first medical image data set and an individual slice of the third medical image data set. Accordingly, more than two medical image data sets may be synchronized. Any explanations provided in connection with the second medical image data set can equally be applied to the at least one third medical image data set.

According to some examples, the method may comprise: identifying one or more reference slices in the first medical image data set, the one or more reference slice respectively comprising one or more prior lesions; identifying, in the at least one third medical image data set the slices respectively corresponding to the identified reference slices based on the step of identifying for each of a plurality of slices of the first medical image data set one corresponding slice of the at least one third medical image data set (or based on the aforementioned association); detecting, in the slices corresponding to the identified reference slices, one or more follow-up lesions; matching the prior lesions with the follow-up lesions identified in the second medical image data set and the at least one third medical image data set; determining a temporal evolution of the detected prior lesions based on the matched follow-up lesions; and providing the temporal evolution.

According to some examples, the first and second medical image data sets at least partially depict the same body part of different patients. Thus, the method enables to synchronize and compare medical studies of different patients. This may offer, e.g., the possibility to compare the traget patient to a reference patient showing pathological conditions similar to the target patient.

According to some examples, first and second medical image data sets respectively comprise magnetic resonance image data. The first medical image data set has been acquired using a first magnetic resonance imaging protocol and the second medical image data set has been acquired using a second magnetic resonance imaging protocol different to the first magnetic resonance imaging protocol.

In other words, the method foresees to compare medical image data sets having been acquired using different imaging protocols for magnetic resonance imaging. This has the advantage that complementary insights acquired with different imaging protocols can directly be compared side-by-side. For instance, the first medical image data set may have been acquired using a first magnetic resonance pulse sequence, and the second medical image data set may have been acquired using a second magnetic resonance pulse sequence functionally different to the first magnetic resonance pulse sequence.

"Functionally different" in this context may mean that for first and second magnetic resonance pulse sequences different parameters and conditions may apply. This may amount to different physical parameters adjusted at the MR imaging modality as well as to a controlled adjustment of different physiological conditions of the patient. For instance, the first medical image data set may have been acquired using a T1 sequence while the second medical image data set has been acquired using a T2 sequence or vice versa. The usage of two functionally different MR pulse sequences in combination with synchronizing the medical image data sets makes it possible to gather additional information by observing how one and the same region behaves for different sequences. In particular, additional information may be gleamed by analyzing the way in which a region absorbs and washes out a magnetic contrast agent. To this end, the second magnetic resonance pulse sequence may be a post-contrast sequence after a contrast agent has been administered to the patient while the first pulse sequence relates to a pre-contrast sequence before the contrast agent has been administered to the patient. Alternatively, first and second pulse sequences may relate to different post-contrast sequences, i.e., sequences acquired at different points in time after a contrast agent has been administered to the patient. Post-contrast MR sequences may include a T1 relaxation sequence that is well suited for monitoring the absorption and washout of magnetic contrast agents. As yet a further example, the second pulse sequence may be a so-called double inversion recovery sequence using two non-selective 180°-inverting pulses. As such, double inversion recovery is a technique for suppressing signal from specific tissue or fluid types and can be used to make certain lesions more apparent and/or to not only show new but also active lesions.

According to some examples, the first medical image data set has been acquired using a first medical imaging modality and the second medical image data set has been acquired using a second medical imaging modality, wherein the first medical imaging modality is based on an imaging technology different from the imaging technology the second modality is based on. The first modality is preferably based on an x-ray imaging technology, in particular, a computed tomography imaging technology, and the second modality is preferably based on a magnetic resonance imaging technology.

In other words, the method enables synchronizing medical image data sets acquired with functionally different imaging modalities.

According to some examples, the first medical image data set comprises a two-dimensional key image indicative of at least one finding previously reported for a patient, and the second medical image data set optionally is an image series the key image has been extracted from upon reporting the at least one finding for the patient.

According to these examples, the method enables to retrieve the slice a key image has been extracted from. In turn, this allows the user to inspect the slices surrounding the key image, e.g., in order to infer the extension of a lesion in a direction perpendicular to the image plane of the key image.

According to some examples, the method may comprise identifying, from a plurality of slices comprised in the second medical image data set, for the key image, a plurality of corresponding slices. In other words, the method retrieves a plurality of candidate corresponding slices coming into question as the corresponding slice of the key image. According to some examples, the candidate corresponding slices are subsequent slices in the second medical image data set. In other words, the candidate corresponding slices belong to the same "slab" within the second medical image data set. According to some examples, the candidate corresponding slices are displayed to the user, e.g., using an appropriate user interface.

By retrieving a plurality of candidate corresponding slices, the method makes allowance to the fact, that several slices may come into question as the slice corresponding to the key image. By identifying them as candidate corresponding slices, the method may bring all of them to the attention of the user who may then make a further selection.

According to some examples, the method further comprises resampling the second medical image data set based on the first medical image data set in order to define a plurality of slices in the second medical image data set.

The resampling is equally applicable to medical image data sets already having slices defined therein and medical image data sets more or less depicting an isotropic image volume without any defined slices. According to some examples, resampling may comprise defining slices in the second medical image data set such that the slices have a slice thickness corresponding to a slice thickness of the first medical image data set. Additionally or alternatively, a stacking direction of the slices may be set or adapted such that it corresponds to the first medical image data set. By resampling the second medical image data set, the second medical image data set may thus be adapted to the first medical image data set. Thereby, the comparability of the two data sets may be improved yielding an overall better result in terms of the ensuing identification of corresponding slices.

According to some examples, the step of identifying the at least one corresponding slice comprises applying a trained function on the first and second medical image data sets, the trained function being adapted to identify corresponding slices in different medical image data sets. In particular, the trained function may be configured to determine a similarity between two-dimensional medical images.

Trained functions, in general, may be seen as mapping input data to output data thereby fulfilling a certain learned task. According to some examples, the trained function may be configured to carry out one or more of the following tasks: respectively extract one or more image descriptors from first and/or second medical image data sets, compare one or more image descriptors, apply a similarity metric, determine one or more degrees of similarity and/or directly identify corresponding slices. The relation between input and output may be governed by one or more (in general: a plethora) of parameters embedded in the trained functions. The values of the parameters may be learned (adapted) during training according to the task, the trained function will have to fulfill. Other terms for trained function may be trained mapping specification, mapping specification with trained parameters, function with trained parameters, trained machine learned model, algorithm based on artificial intelligence, or machine learned algorithm. Applying trained functions may mean inputting the first and second medical image data sets into the trained function.

According to some examples, the trained function comprises a machine learned (artificial) neural network, most preferably a convolutional neural network. A neural network is basically built up like a biological neural net, e.g., a human brain. In particular, an artificial neural network comprises an input layer and an output layer. It may further comprise a plurality of layers between input and output layer. Each layer comprises at least one, preferably a plurality of nodes. Each node may be understood as a biological processing unit, e.g., a neuron. In other words, each neuron corresponds to an operation applied to input data. Nodes of one layer may be interconnected by edges or connections to nodes of other layers, in particular, by directed edges or connections. These edges or connections define the data flow between the nodes of the network. In particular, the edges or connections are equipped with a parameter, wherein the parameter is often denoted as "weight". This parameter can regulate the importance of the output of a first node to the input of a second node, wherein the first node and the second node are connected by an edge. In particular, a neural network can be trained. In particular, training of a neural network is performed based on known pairs of input and output values according to a 'supervised learning' technique, wherein the known input values are used as inputs of the neural network, and wherein the corresponding output value of the neural network is compared to the corresponding known output value. The artificial neural network independently learns and adapts the weights for the individual nodes as long as the output values of the last network layer sufficiently correspond to the known output values according to the trainings data. For convolutional neural networks, this technique is also called 'deep learning'. The terms 'neural network' and 'artificial neural network' can be used as synonyms.

A first group of neural network layers may be applied to extract features from the image data comprised in the first and second medical image data sets, in particular, from respective slices and/or key images of first and second medical image data sets. Image data may, for instance, be given in the form of the gray scale and/or color values of each slice/image. The thus extracted features like, contrast, gradients, texture, density, distortion, singularities, patterns, landmarks, masks or the like may form an image descriptor of the respective image/slice. The image descriptors may be fed as input values to a second group of network layers which serve to determine a degree of similarity between two slices or a slice and a key image based on the extracted features. However, both functions of the described neural network may likewise be carried out by separated, individual neural networks. In other words, image analysis for feature extraction can be carried out by a first neural network, and classification according to similarity, i.e., object and/or characteristic assignment, can be carried out by a second neural network.

In particular, the machine learned neural network may be a convolutional neural network. In particular, the machine learned neural network may be a deep convolutional neural network. According to such implementations, the machine learned neural network comprises one or more convolutional layers and/or one or more deconvolutional layers. Further, the machine learned neural network may comprise one or more pooling layers and/or one or more up-sampling layers. Further, the machine learned neural network may comprise one or more fully connected layers.

The inventors have recognized that, through the use of convolutional layers and/or deconvolutional layers, a neural network can be employed especially efficiently for image processing, since despite many connections between node layers, only a few edge weights (namely the edge weights corresponding to the values of the convolutional kernel) have to be determined by training. With a same number of training data, the accuracy of the neural network can thus also be improved.

According to some examples, the trained function comprises a distance metric learning network and, in particular, a deep distance metric learning network.

Distance metric learning (or simply, metric learning) aims at automatically constructing task-specific distance or similarity metrics from supervised data, in a machine learning manner. The learned distance metric can then be used to perform various tasks such as, in this case, the identification of similar slices. In comparison to the usage of preset distance metrics, learned distance metrics may have the advantage that the learned metric is better adapted to the particular data and task of interest.

Deep distance metric learning networks may additionally transform the data into a new feature space with higher discrimination power before a metric (either learned or standard) is applied. The feature space may be such that extracted image features that are semantically similar are mapped onto nearby locations while dissimilar image features are pushed apart using an appropriate distance metric.

According to some examples, the trained function comprises a Siamese network. According to further examples, the trained function may comprise a fully convolutional Siamese network.

A Siamese network is a type of neural network that learns to compare two inputs based on a distance or similarity metric such that inputs that are closer in some semantics get a lower distance in comparison to two inputs that are further apart according to the same semantics. The semantics that need to be captured is fed to the network implicitly during the training processes. The semantics can be conceived as the vector space of the image descriptors. Accordingly, the semantics determine which image descriptors are extracted. The semantics may be extracted using branches of subnetworks with identical structure and parameters. The extracted image descriptors may be seen as a representation of the learned semantic. In particular, a Siamese network may comprise a structure with two branches of sub-networks with identical structure and parameters.

Based on a fully convolutional Siamese network at least one convolution processing and at least one pooling processing may be executed on, e.g., a first slice of the first image data set, thus obtaining image features (or the image descriptor) of that first image slice. Further, at least one convolution processing and at least one pooling processing may be executed on, e.g., a second slice of the second image data set, thus obtaining image features (or the image descriptor) of that second image slice. The output image features (or image descriptors) after convolution processing and pooling processing may be one or more feature vectors or maps with the same size. Parameters in the convolution processing or the pooling processing, for example, the sizes and number of convolution kernels used for each convolution layer or each pooling layer may be preconfigured via the training process of the fully convolutional Siamese network. In particular, also a fully convolutional Siamese network may comprise a structure with two branches of sub-networks with identical structure and parameters.

According to some examples, the trained function comprises a triplet network.

Triplet networks may be conceived as an extension of Siamese networks, as triplet networks may comprise three branches of the same feedforward network. When fed with three samples, the network outputs intermediate values in the form of a pair of distances. Thereby, one sample is taken as the reference (or anchor) against which the others are compared. The intermediate values are then fed into a comparator to determine an output. Rather than directly comparing data labels, the triplet network allows learning by comparison of samples which poses lower requirements to the training data and could enable the usage as an unsupervised learning model.

According to some examples, the trained function is trained using a triplet loss function.

A triplet loss function is a loss function for machine learning algorithms where a reference (anchor) input is compared to a positive (truthy) input and a negative (falsy) input. The distance from the baseline (anchor) input to the positive input is minimized, and the distance from the reference input to the negative input is maximized. Transferred to the present case, the positive input could be a slice with verified similarity to a given reference slice. The similarity can, for instance, be verified by a user or be due to an verified adjacency of the slice to the reference slice in an image study. The latter has the advantage that training data can be obtained rather easily. The negative input may for instance be a slice that is less similar to the reference slice than the positive input. In particular, the negative input may be a slice that is not related to the reference slice, e.g., a slice from a different study or patient. By enforcing such an order of similarities, triplet loss models embed (i.e., extract image descriptors) in a way that a pair of similar slices are smaller in distance (or have a higher degree of similarity) than dissimilar slices. One advantage of this approach is that triplet loss functions are very flexible in terms of the training data required.

As an alternative, also other loss functions may be used, such as contrastive loss functions which are computed by contrasting two or more degrees of similarity of slice pairs, or categorical cross-entropy loss functions.

According to an aspect, a computer-implemented method for providing a trained function is provided. The method comprises a plurality of steps. One step is directed to receiving a trained function. A further step is directed to providing a first slice image, a second slice image, and a third slice image, wherein first second and third slice images have been extracted from one or more medical image studies and the second slice image has a greater similarity to the first slice image than the third slice image to the first slice image. A further step is directed to inputting the first, second and third slice images into the trained function. A further step is directed to determine a first degree of similarity between the first slice image and the second slice image and a second degree of similarity between the first slice image and the third slice image. A further step is directed to adjusting the trained function such that first degree of similarity is greater than the second degree of similarity.

In other words, the first slice image is used as anchor, while the second slice image is used as positive example and the third slice image is used as negative example. First and second degrees of similarity may, for instance, relate to the distance in feature space between the image descriptors respectively extracted from the three slice images by the trained function. Adaptations to the trained function may, for instance, concern what kind of image descriptors are extracted and/or how the extracted image descriptors are compared/processed to derive a degree of similarity. The proposed learning scheme has the advantage that it is less demanding as regards the quality of the training data. Specifically, it does not require absolute labels as to the degrees of similarity which in most cases would be very difficult to provide. Rather, weak labels in the form of a relative indication which one of two slice images is more similar to a comparative slice are sufficient to adjust the trained function. Such weak labels are implicitly comprised in any image study comprising a plurality of slices: starting form an arbitrary slice, a neighboring slice will (in most cases) be more similar to the selected slice than a more distant one. According to some examples, first, second and third slices are therefore extracted from the same medical image study.

According to an aspect, a computer-implemented method for identifying corresponding slices in medical image data sets, is provided. The method comprises a plurality of steps. One step is directed to receiving a two-dimensional reference image indicative of at least one finding previously reported for a patient. A further step is directed to retrieving a first medical image data set corresponding to the reference image. A further step is directed to identifying, from a plurality of slices of the first medical image data set, at least one corresponding slice with respect to the reference image based on degrees of similarity between the reference image and individual slices of the first medical image data set so as to provide a first assignment between the reference image and a corresponding slice in the first medical image data. A further step is directed to receiving a second medical image data set, the second medical image data set at least partially depicting the same body part of the patient as the first medical image data set but having been acquired at a different point in time as compared to the first medical image data set. A further step is directed to identifying, for each of a plurality of slices of the first medical image data set one corresponding slice of a plurality of slices of the second medical image data set, the degrees of similarity being respectively based on a similarity between an individual slice of the first medical image data set and an individual slice of the second medical image data set so as to provide a second assignment between slices of the first medical image data set and slices of the second medical image data set. A further step is directed to selecting at least one slice from the second medical image data set based on the first assignment and on the second assignment so as to provide a selected slice, the selected slice corresponding to the reference image based on the determined degrees of similarity.

The above method reflects an image reading workflow for follow-up reading where the user is confronted with the task to determine a disease progression based on a reference image. Through the execution of two slice matching steps, the user is automatically provided with the slice in the second medical image data set he is likely supposed to review. At the same time, first and second medical data sets are being synchronized. Compatibility provided, all further aspects and examples disclosed herein can be used to modify the above method. Explanations and advantages disclosed in this respect can likewise be transferred to the above method. In particular, degrees of similarity may be calculated using a trained function.

According to a further aspect, a computer-implemented method for determining a comparability of two medical image data sets is provided. The method comprises a plurality of steps. One step is directed to receiving a first medical image data set. Another step is directed to receiving a plurality of second medical image data sets, wherein first and second medical image data sets have been acquired from the same patient at different points in time, respectively. For each second medical image data set the method further comprises identifying slices having a corresponding slice in the first medical image data set as overlapping slices by determining degrees of similarity between individual slices of the first medical image data set and the respective second medical image data set, wherein each degree of similarity is based on a similarity of an individual slice of the first medical image data set and an individual slice of the respective second medical image data set, and determining an anatomical overlap between the image volume of first medical image data set and the image volume of the respective second medical image data set based on the overlapping slices. Another step is directed to determining a degree of comparability of each of the second medical image data sets with the first medical image data set based on the determined anatomical overlaps. Another step is directed to providing the determined degrees of comparability to a user via a user interface.

The above method applies the similar slice search scheme to automatically evaluate whether or not two image studies of a patient are suited for direct comparison during follow-up reading. The degrees of comparability may be indicated to the user together with the available second medical image data sets. This spares the user the tedious job of loading and opening the available studies one-by-one in order to see whether they are suited for follow-up reading. Specifically, the first medical image data set may relate to a follow-up image study of a body part of the patient, while the second medical image data sets may relate to the prior image studies available for the patient which have been taken at an earlier point in time.

According to some examples, the method further comprises selecting one or more medical image data sets from the second medical image data sets based on the determined anatomical overlaps and providing the selected second medical image data sets to a user.

Accordingly, the second medical image data sets coming into question for follow-up reading are automatically pre-selected and presented to the user. From these pre-selected second medical image data sets the user may then pick those which he considers most relevant. Due to the pre-selection, the user can be sure that all of the provided second medical image data sets offer a reasonable basis for comparison with the first medical image study. According to some examples, selecting one or more medical image data sets from the second medical image data sets comprises selecting those medical image data sets the anatomical overlap of which is larger than a predetermined threshold. The threshold can, e.g., be provided in the form of a minimal number of corresponding slices or in the form of a minimal image volume two image studies have to have in common.

According to an aspect, a system for identifying corresponding slices of medical image data sets is provided. The system comprises an interface for receiving a first medical image data set and a second medical image data set different from the first medical image data set. Further, the system comprises a computing unit configured to identify, from a plurality of slices comprised in the second medical image data set, at least one corresponding slice based on degrees of similarity between the image data comprised in the first medical image data set and individual slices of the second medical image data set.

According to an aspect, a system for determining a degree of comparability of medical image data sets is provided. The system comprises an interface for receiving a first medical image data set and a plurality of second medical image data set different from the first medical image data set, first and second medical image data sets having been acquired from the same patient at different points in time, respectively. The system further comprises a computing unit. The computing unit is configured to, for each second medical image data set, identify those slices having a corresponding slice in the first medical image data set as overlapping slices by determining degrees of similarity between individual slices of the first medical image data set and the respective second medical image data set, wherein each degree of similarity is based on a similarity of an individual slice of the first medical image data set and an individual slice of the respective second medical image data set. Further, the computing unit is configured to, for each second medical image data set, determine an anatomical overlap between the image volume of first medical image data set and the image volume of the respective second medical image data set based on the overlapping slices. Further, the computing unit is configured to determine a degree of comparability for each of the second medical image data sets with the first medical image data set based on the determined anatomical overlaps.

According to an aspect, a system for identifying corresponding slices in medical image data sets is provided. The system comprises an interface for receiving a two-dimensional key image indicative of at least one finding previously reported for a patient, for retrieving a first medical image data set corresponding to the reference image, and for receiving a second medical image data set, the second medical image data set at least partially depicting the same body part of the patient as the first medical image data set but having been acquired at a different point in time than the first medical image data set. Further, the system comprises a computing unit. The computing unit is configured to retrieve the first medical image data set based on the reference image via the interface. The computing unit is configured to identify, from a plurality of slices of the first medical image data set, at least one corresponding slice with respect to the reference image based on degrees of similarity between the reference image and individual slices of the first medical image data set so as to provide a first assignment between the reference image and a corresponding slice in the first medical image data. The computing unit is configured to identify, for each of a plurality of slices of the first medical image data set, one corresponding slice of a plurality of slices of the second medical image data set by evaluating similarities between the first and second medical image data sets using the trained function so as to provide a second assignment between slices of the first medical image data set and slices of the second medical image data set. The computing unit is configured to select at least one slice from the second medical image data set based on the first assignment and on the second assignment so as to provide a selected slice, the selected slice having a certain degree of similarity to the key image.

According to some examples, the above systems are adapted to implement the corresponding inventive methods. In particular, the computing units may be configured to run a trained function configured to determine similarities between two-dimensional medical images. The computing units may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processor, one or more memories and combinations thereof. The one or more memories may store instructions for carrying out the method steps according to example embodiments of the present invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interfaces may comprise an interface for data exchange with a local server or a central web server via internet connection for receiving first and second medical image data sets and further information such as key images. The interfaces may be further adapted to interface with one or more users of the system, e.g., by displaying the result of the processing by the computing unit to the user (e.g., in a graphical user interface) or by allowing the user to adjust parameters and/or to select first and second medical image data sets.

According other aspects, example embodiments of the present invention further relates to image analysis systems comprising the above systems and a medical image system (or medical information system) configured to acquire, store and/or forward first and second medical image data sets and further information such as key images. Thereby, the interface is configured to receive the first and second medical image data sets and further information such as key images from the medical image system.

According to some examples, the medical image system comprises one or more archive stations for storing first and second medical image data sets which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another aspect, example embodiments of the present invention further relates to a training system for providing a trained function. The system comprises an interface embodied for receiving a trained function and further embodied for receiving a first two-dimensional medical image, a second two-dimensional medical image, and a third two-dimensional medical image. Thereby first second and third medical images have been extracted from one or more medical image studies respectively depicting image volumes of body parts of patients and the second medical image has a greater similarity to the first medical image than the third medical image has to the first medical image. The system further comprises a computing unit configured to run the trained function. The computing unit is further configured to input the first, second and third medical images into the trained function, to determine a first degree of similarity between the first medical image and the second medical image and a second degree of similarity between the first medical image and the third medical image, to adjust the trained function such that first degree of similarity is greater than the second degree of similarity, and to provide the adjusted trained function.

In particular, such a training system can be embodied for carrying out the inventive method for providing a trained function and its aspects previously described. The training system is embodied to carry out this method and its aspects, in that the interface and the computing unit are embodied to carry out the corresponding method steps.

The training system's computing unit may in particular involve a computer, a microcontroller or an integrated circuit. As an alternative the training system may involve a real or virtual network of computers (a real network is referred to as a cluster, a virtual network is referred to as a cloud). The interface may involve a hardware or software interface (for example PCI-Bus, USB or Firewire).

According to another aspect, the present invention is directed to a computer program product comprising program elements which induce a computing unit of a system for quantifying a medical image volume to perform the steps according to the above method, when the program elements are loaded into a memory of the computing unit.

According to another aspect, the present invention is directed to a computer-readable medium on which program elements are stored that are readable and executable by a computing unit, in order to perform steps of the inventive methods, when the program elements are executed by the computing unit.

The realization of example embodiments of the present invention by a computer program product and/or a computer-readable medium has the advantage that already existing providing systems can be easily adopted by software updates in order to work as proposed by example embodiments of the present invention.

The computer program product can be, for example, a computer program or comprise another element next to the computer program as-such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

FIG. 1 depicts a system 1 for identifying corresponding slices in medical image data sets MIDS-1, MIDS-2. In this regard, system 1 is adapted to perform the methods according to one or more embodiments, e.g., as further described with reference to FIGS. 2 to 10. A user of system 1, according to some examples, may generally relate to a healthcare professional such as a physician, clinician, technician, radiologist, pathologist and so forth. According to some examples, the group of users explicitly does not involve a target patient.

System 1 comprises a user interface 10 (as part of the interface) and a processing system 20 (as part of the computing unit 30). Further, system 1 may comprise or be connected to a medical information system 40. The medical information system 40 may generally be configured for acquiring and/or storing and/or forwarding medical image data sets MIDS-1, MIDs-2. For instance, medical information system 40 may comprise one or more archive/review station (not shown) for storing medical image data sets MIDS-1, MIDs-2. The archive/review stations may be embodied by one or more databases. In particular, the archive/review stations may be realized in the form of one or more cloud storage modules. Alternatively, the archive/review stations may be realized as a local or spread storage, e.g., as a PACS (Picture Archiving and Communication System). Further, the archive/review stations may further store additional clinical information related to medical image data sets MIDS-, MIDS-2, wherein the clinical information may comprise, e.g., related medical findings, key images prepared during a prior inspection of the patient case, one or more prior (structured) medical reports, personal information related to the patient under consideration, patient records or the like. According to some examples, medical information system 40 may also comprise one or more medical imaging modalities (not shown), such as a computed tomography system, a magnetic resonance system, an angiography (or C-arm X-ray) system, a positron-emission tomography system, a mammography system, system for acquiring digital pathology images or the like.

Medical image data sets MIDS-1, MIDS-2 may be three-dimensional image data sets acquired, for instance, using a computed tomography system or a magnetic resonance imaging system or other systems. The image information may be encoded in a three-dimensional array of m times n times p voxels. Each medical image data set MIDS-1, MIDS-2 may include a plurality of image slices S-1, S-2 (also denoted just as "slices") which are stacked in a stacking direction to span the image volume covered by the respective medical image data set MIDS-1, MIDS-2.

Further, medical image data sets MIDS-1 may comprise on or more individual two-dimensional medical images with the image information being encoded in an array of m times n pixels. According to some examples, these two-dimensional medical images have been extracted from three-dimensional medical image data sets. In particular, the two-dimensional medical images may comprise so-called key images. Key images may be images which are found to show a particularly remarkable pathology. According to some examples, the two-dimensional images relate to slices extracted from three-dimensional medical image data sets. According to other examples, the two-dimensional medical images have been separately acquired using an appropriate imaging modality.

An ensemble of voxels or pixels may be designated as image data of the respective data set in the following. In general, any kind of imaging modalities and scanners may be used for acquiring such image data, such as ultrasound, x-ray, angiography, fluoroscopy, positron emission tomography, single photon emission computed tomography, or others. Generally, medical image data sets MIDS-1, MIDS-2 show a body part of a patient which may comprise various anatomies and organs. Considering the chest area as a body part, medical image data sets MIDS-1, MIDS-2 might, for instance, depict the lung lobes, the rib cage, the heart, lymph nodes, and so forth. Medical image data sets MIDS-1, MIDS-2 may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as patient's name, ID, etc., and also special attributes containing the image pixel data and meta-data extracted from the image data.

Further, the medical image data sets MIDS-1, MIDS-2 may also comprise non-image data in the form of meta-data. Such meta-data may provide additional information with regard to the image data such as the imaging modalities and protocols used and/or findings or annotations reported or created by a user and so forth. Further, non-image data may comprise information not directly related to the image data such as personal information of the patient such as gender, age, weight, insurance details, information about the treating physician and so forth.

User interface 10 comprises a display unit 11 and an input unit 12. User interface 10 may be embodied by a mobile device such as a smartphone or tablet computer. Further, user interface 10 may be embodied as a workstation in the form of a desktop PC or laptop. Input unit 12 may be integrated in display unit 11, e.g., in the form of a touch screen. As an alternative or in addition to that, input unit 12 may comprise a keyboard, a mouse or a digital pen and any combination thereof. Display unit 11 may be configured for displaying the medical image data sets MIDS-1, MIDS-2. In particular, display unit 11 may be configured to display individual slices of medical image data sets MIDS-1, MIDS-2 and or individual two-dimensional images such as the key images KI.

User interface 10 further comprises an interface computing unit 13 configured to execute at least one software component for serving display unit 11 and input unit 12 in order to provide a graphical user interface (c.f. FIGS. 6 to 9) for allowing the user to select a target patient's case to be reviewed. In addition, interface computing unit 13 may be configured to communicate with medical information system 40 or processing system 20 for receiving the patient data TPD of the target patient and/or the result of clinical decision support procedure. The user may activate the software component via user interface 10 and may acquire the software component, e.g., by downloading it from an internet application store. According to an example, the software component may also be a client-server computer program in the form of a web application running in a web browser. The interface computing unit 13 may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Processing system 20 may comprise sub-units 21-25 configured to process the medical image data sets MIDS-1, MIDS-2 in order to identify corresponding image contents and thereby synchronize two medical image data sets MIDS-1, MIDS-2 with one another, to determine a comparability of two medical image data sets MIDS-1, MIDS-2 based on the identified slice correspondence CS, and/or to derive a temporal evolution of one or more measured values based on the identified slice correspondence CS.

Processing system 20 may be a processor. The processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The processor may be single device or multiple devices operating in serial, parallel, or separately. The processor may be a main processor of a computer, such as a laptop or desktop computer, or may be a processor for handling some tasks in a larger system, such as in the medical information system or the server. The processor is configured by instructions, design, hardware, and/or software to perform the steps discussed herein. Alternatively, processing system 20 may comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the medical image data sets MIDS-1, MIDS-2. Alternatively, such memory may as well be comprised in user interface 10.

Sub-unit 21 is a data retrieval module or unit. It is configured to access and search the medical information system 40 for relevant medical image data sets MIDS-1, MIDS-2. For instance, sub-unit 21 may configured to retrieve all potentially relevant prior examinations of a patient with respect to a follow-up examination currently under review. Further, sub-unit 21 may be configured to retrieve one or more medical image data sets MIDS-1, MIDS-2 corresponding to a key image KI of a patient or vice versa. Specifically, sub-unit 21 may be configured to formulate search queries and parse them to medical information system 40. In particular, sub-unit 21 may be configured to extract data identifiers from the information available and use these for querying medical information system 40.

Sub-unit 22 can be conceived as a slice matching module or unit: It is configured to identify corresponding image data in two or more medical image data sets MIDS-1, MIDS-2. In particular, sub-unit 22 may be configured to identify those slices of a medical image data set MIDS-2 which correspond to a key image KI previously extracted from that medical image data set MIDS-2 or any other two-dimensional medical image. Further, sub-unit 22 may be configured to unambiguously assign corresponding slices of two medical image data sets MIDS-1, MIDS-2 to one another. To this end, sub-unit 22 is configured to quantify an image similarity between individual slices or images of the respective medical image data sets MIDS-1, MIDS-2. According to some examples, sub-unit may be configured to run a trained function TF configured to determine a similarity between two-dimensional medical images.

Sub-unit 23 may be conceived as a comparator module or unit. It is configured to determine to what extend two medical image data sets MIDS-1, MIDS-2 are comparable in terms of the image volumes they depict. Specifically, sub-unit 23 is configured to derive a degree of comparability based on the number of corresponding slices determined by sub-unit 22.

Sub-unit 24 is a measurement module or unit. It is configured to use the information about corresponding slices provided by sub-unit 22 to perform comparative measurements on image features comprised in two or more medical image data sets MIDS-1, MIDS-2 (which have been "synchronized" by way of the identified slice correspondence CS). Specifically, sub-unit 24 may be configured to detect lesions in the medical image data sets MIDS-1, MIDS-2 and match the detected lesions across the medical image data sets MIDS-1, MIDS-2 using the information about mutually corresponding slices as provided by sub-unit 22. For detecting lesions in medical image data sets, sub-unit 24 may be configured to run appropriate computer-aided detection algorithms.

Sub-unit 25, may be conceived as a synchronized viewing module or unit. Sub-unit 25 may be configured to allow for a synchronized viewing and, in particular, scrolling of two medical image data sets MIDS-1, MIDS-2 (which have been "synchronized" by way of the identified slice correspondence CS). To this end, dub-unit 25 may be configured to receive inputs from a user indicating the selection of a particular slice of one of the two medical image data sets MIDS-1. On that basis and using the information about the mutually corresponding slices provided by sub-unit 22, sub-unit 25 may be configured to determine which slice of the respective other medical image data set MIDS-1 corresponds to the user-selected slice. Sub-unit 25 may further be configured to display the user-selected slice and the slice corresponding thereto in an appropriate graphical user interface.

The designation of the distinct sub-units 21-25 is to be construed by way of example and not as limitation. Accordingly, sub-units 21-25 may be integrated to form one single unit (e.g., in the form of "the computing unit 30") or can be embodied by computer code segments configured to execute the corresponding method steps running on a processor or the like of processing system 20. The same holds true with respect to interface computing unit 13. Each sub-unit 21-25 and interface computing unit 13 may be individually connected to other sub-units and or other components of the system 1 where data exchange is needed to perform the method steps. For example, sub-units 21 and 25 may be connected via an interface 26 to medical information system 40 for retrieving medical image data sets MIDS-1, MIDS-2. Likewise, interface 26 may connect the sub-units 21 to 25 to interface computing unit 13 for forwarding the results of the computation to the user and collect user inputs.

Processing system 20 and interface computing unit 13 together may constitute the computing unit 30. Of note, the layout of computing unit 30, i.e., the physical distribution of interface computing unit 13 and sub-units 21-25 is, in principle, arbitrary. For instance, sub-unit 25 (or individual elements of it or specific algorithm sequences) may likewise be localized in user interface 10. The same holds true for the other sub-units 21-24. Specifically, processing system 20 may also be integrated in user interface 10. As already mentioned, processing system 20 may alternatively be embodied as a server system, e.g., a cloud server, or a local server, e.g., located on a hospital or radiology site. According to such implementation, user interface 10 could be designated as "frontend" or "client" facing the user, while processing system 20 could then be conceived as "backend" or server. Communication between user interface 10 and processing system 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Individual components of system 1 may be at least temporarily connected to each other for data transfer and/or exchange. User interface 10 communicates with processing system 20 via interface 26 to exchange, e.g., patient data TPD, data descriptors or the result of the computation. For example, processing system 20 may be activated on a request-base, wherein the request is sent by user interface 10. Further, processing system 20 may communicate with medical information system 50 in order to retrieve a target patient's case. As an alternative or in addition to that, user interface 10 may communicate with medical information system 40 directly. Medical information system 40 may likewise be activated on a request-base, wherein the request is sent by processing system 20 and/or user interface 10. Interface 26 for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Interface 26 for data exchange together with the components for interfacing with the user 11, 12 may be regarded as constituting an interface unit of system 1.

Figure 2:
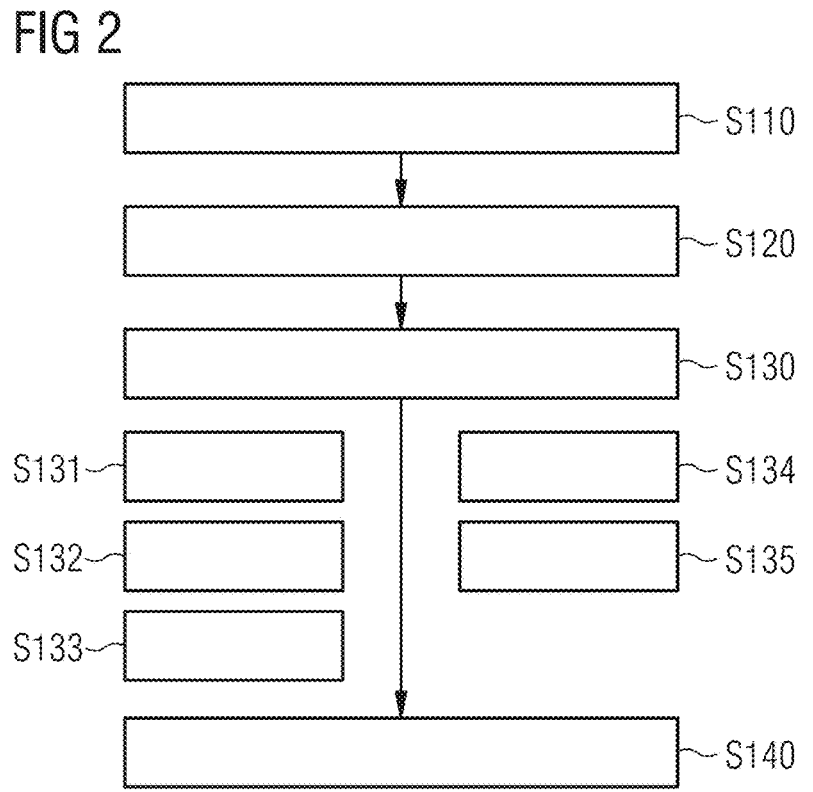
FIG. 2 depicts a flowchart illustrating a method for identifying corresponding slices of medical image data sets according to an embodiment, FIG. 3 schematically shows data streams associated with a method for identifying corresponding slices of medical image data sets according to the corresponding embodiment.
Figure 3:
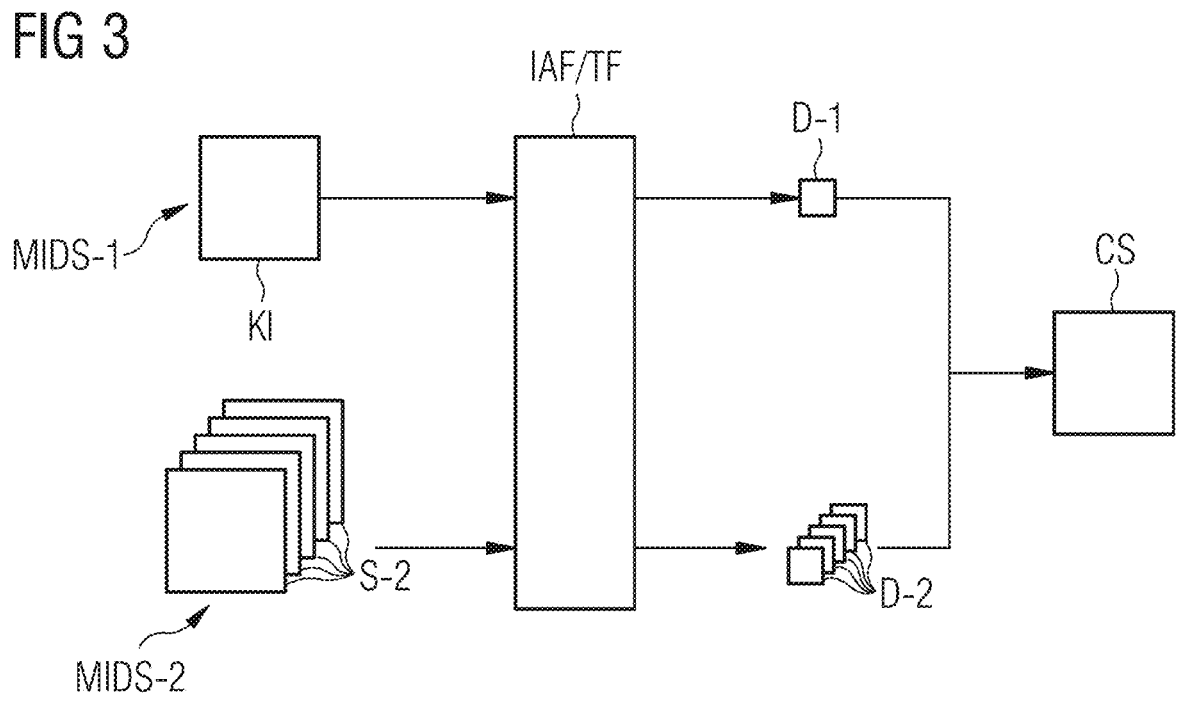

FIG. 2 depicts a method for identifying corresponding slices of medical image data sets MIDS-1, MIDS-2 according to an embodiment of the present invention. Corresponding data streams are illustrated in FIG. 3. The method comprises several steps. The order of the steps does not necessarily correspond to the numbering of the steps but may also vary between different embodiments of the present invention. Further, individual steps or a sequence of steps may be repeated.

In a first step S110, the first medical image data set MIDS-1 is received. In the embodiment of FIGS. 2 and 3, the image data comprised in the first medical image data set MIDS-1 relates to a two-dimensional image of a body part of a patient. The two-dimensional image may have been acquired using one of the imaging modalities mentioned above. In particular, the two-dimensional image may be an image which has been extracted from a previous image study of the patient. Further, the two-dimensional image may be a so-called key-image KI which has been generated from a previous study and/or has been included in a corresponding medical report. Step S110 may involve manually selecting the patient case by the user with the user interface 10 and/or retrieving the first medical image data set MIDS-1 from the medical information system 50. Further, step S110 may involve automatically selecting the first medical image data set MIDS-1 based on the case and the task at hand. Additionally, the first medical image data set MIDS-1 may be selected based on the second medical image data set MIDS-2. For instance, a user may select the second medical image data set MIDS-2 and step S110 may then comprise automatically retrieving an appropriate first medical image data set MIDS-1 which could be useful for reading the second medical image data set MIDS-2. To this end, a data identifier, such as a patient or case ID, may be extracted from the second medical image data set MIDS-2 and used to query the medical information system 40 for appropriate associated information. Step S110 may be performed at least partially either on user interface 10 or on processing system 20. Corresponding data exchange is included in this step where necessary.

In a further step S120, the second medical image data set MIDS-2 is received. This may involve selecting the second medical image data set MIDS-2 from a plurality of available data sets of a patient which may be stored in the medical information system 40. The selection may be performed manually by a user, e.g., by selecting appropriate image data sets MIDS-2 in a graphical user interface running in the user interface 10. Moreover, the selection may be carried out automatically or semi-automatically by the system for users which need more assistance. In particular, this may involve automatically querying connected databases for appropriate image data sets, in particular, based on the first medical image data set MIDS-1. According to this embodiment, the second medical image study MIDS-2 depicts an image volume of the patient. Accordingly, it relates to three-dimensional image data. The second medical image data set MIDS-2 may comprise several image slices S-2 stacked in a slice direction to span the image volume. According to other examples, the second medical image data set may be isotropic without already comprising defined slices. According to some examples, the second medical image data set MIDS-2 may be the image study, from which the image data of the first medical image data set MIDS-1, i.e., the key image KI, has been extracted. Step S120 may be performed at least partially either on user interface 10 or on processing system 20. Corresponding data exchange is included in this step where necessary.

Step S130 is concerned about identifying corresponding image information in the first and second medical image data sets MIDS-1, MIDS-2 to support the user in the comparative reading of these data sets. In the use case of FIGS. 2 and 3, step 130 would thus identify the image data in the second medical image data set MIDS-2 which shows the greatest correspondence with the image data of the first medical image data set MIDS-1. In particular, this may involve identifying the slice or the slices of the second medical image data set MIDS-2 showing the highest degree of similarity with the key image KI comprised in the first medical image data set MIDS-1.

In the following, steps S131 to S135 set out some exemplary embodiments, how the identification of corresponding image data of step S130 may be put into practice. They provide several examples in this regard but are not to be considered as limiting the scope of step S130 as they do not exclude further possibilities how a similarity between image data sets can be determined. For instance, as an alternative to an explicit extraction of image descriptors D-1, D-2 and their ensuing comparison, a Fourier-based analysis scheme may be implemented. Here, individual images or image regions would be transformed into the Fourier space and a similarity would be calculated by applying mathematical convolution functions. The image processing of step S130 (and all optional steps) may predominantly be performed on processing system 20.

An optional step S131 is directed to resampling the second medical image data set MIDS-2 based on the first medical image data set MIDS-1 for bringing it into a better shape for the ensuing comparison of the image contents of the two data sets. This may involve defining a plurality of slices S-2 of appropriate slice thickness and stacking direction in the second medical image data set MIDS-2. This may further involve resampling already existing slices S-2 in the second medical image data set MIDS-2 such that they have an appropriate slice thickness and orientation. Moreover, step S131 may comprise other image processing steps for improving the comparability of the second medical image data set MIDS-2 with the first medical image data set MIDS-1. This may comprise reading the image processing steps done to the image data comprised in the first medical image data set MIDS-1 (which may be encoded in a metadata file of the first medical image data set MIDS-1, for instance) and applying the same image processing steps to the second medical image data set MIDS-2.

A further optional step S132 is directed to providing a trained function TF which is configured to determine and, in particular, quantify an image similarity between two-dimensional medical images. In particular, the trained function may be configured to carry out the subsequent steps S133-S135. It is to be understood, however, that the subsequent steps S133-S135 may also be carried out without the use of trained functions, i.e., by image analysis functions IAF with hard-coded functionalities which implement one or more deterministic rules, e.g., for selecting features from image data and determining degrees of similarity on that basis.

At step S133, an image descriptor D-1 is generated from the first medical image data set MIDS-1, i.e., the two-dimensional key image KI therein comprised. The image descriptor D-1 may comprise the representative or characterizing features of the key image KI in the form of a feature vector. Since the first medical image data set MIDS-1 may generally comprise image data as well as non-image data, the image descriptor D-1 may likewise be based on image feature signatures and non-image features. Image feature signatures may be generated by image analysis methods comprising the identification, analysis and/or measurement of objects, local and or global structures and/or textures present in any image data comprised in the first medical image data set MIDS-1. The generated image feature signatures may comprise an anatomical feature and/or structure, like e.g. the presence of a landmark or the size of an organ or a structure, texture and/or density of an identified tissue or organ and so forth. The image feature signatures may likewise comprise a parameter characterizing a color and/or grey scale scheme or contrast characteristics or local gray scale gradients present in the analyzed image. The image feature signatures preferably comprise not only one but numerous features which as a sum characterize the analyzed image. The non-image features extracted from the non-image data comprised in the first medical image data set MIDS-1 may comprise meta-data associated to the image data. Further, they may relate to data independent form the image data providing further context information with regard to the target patient, such as features extracted from the electronic health record, laboratory data, and the like.

At step S134 corresponding image descriptors D-2 are extracted from the second medical image data set MIDS-2. The image descriptors D-2 of the second medical image data set MIDS-2 may be generated in the same way as the image descriptor(s) D-1 for the first medical image data set MIDS-2. According to some examples, the image descriptors D-2 of the second medical image data set MIDS-2 already have been generated before and are stored together with the second medical image data set MIDS-2 in medical information system 40.

At step S135 of FIG. 2, the image descriptor D-1 extracted from the first medical image data set MIDS-1 is compared to the image descriptors D-2 extracted from the second medical image data set MIDS-2. According to some examples, the comparison of steps S135 may comprise determining a similarity or distance metric representing a similarity between the image descriptor D-1 of the first medical image data set MIDS-1 and a respective one of the image descriptors D-2 extracted from the second medical image data set MIDS-2. In some examples, the similarity metric may be a distance in vector space between the image descriptor D-1 of the first medical image data set MIDS-1 and the respective one of the image descriptors D-2 of the second medical image data set MIDS-2. For example, the distance may be the Euclidean distance between the two points in vector space that the respective image descriptors D-1, D-2 represent. In some other examples, the similarity metric may be based on the L1 norm of the respective image descriptors D-1, D-2. In some further examples, other similarity metrics may be used, such as a cosine similarity between the data descriptors D-1, D-2. For each slice S-2 of the second medical image data set MIDS-2 taken into account, the similarity metric may represent how similar the slice S-2 is to the key image KI. In other words, the similarity metric expresses (quantifies) a degree of similarity between the key image KI and a respective slice S-2 of the second medical image data set MIDS-2. The similarities determined in step S135 may be used to select the slice S-2 or those slices S-2 of the second medical image data set MIDS-2 having the greatest similarity to the image data in the first medical image data set MIDS-1, that is the key image KI according to this embodiment. The slice S-2 or the slices S-2 identified in step S130 may be called corresponding slice or slices CS. According to some examples a plurality of similar slices S-2 may be identified as corresponding slices CS. According to other examples, only the slice having the greatest similarity to the key image KI may be identified as the corresponding slice CS of the second medical image data set MIDS-2.

At optional step S140, the identified slices S-2 of the second medical image data set MIDS-2 are provided. This may mean that these corresponding slices are stored in conjunction with the first medical image data set MIDS-1.

Further this may mean that an association is determined electronically linking the respective corresponding slice or slices S-2 of the second medical image data set MIDS-2 to the first medical image data set MIDS-1, which association may, for instance, be used in ensuing optional processing steps. Further, the corresponding slice or slices CS may be displayed to the user via user interface 10 so that the user may directly compare the retrieved corresponding slice or slices CS with the key image KI. Step S140 may be performed at least partially either on user interface 10 or on processing system 20. Corresponding data exchange is included in this step where necessary.

Figure 4:
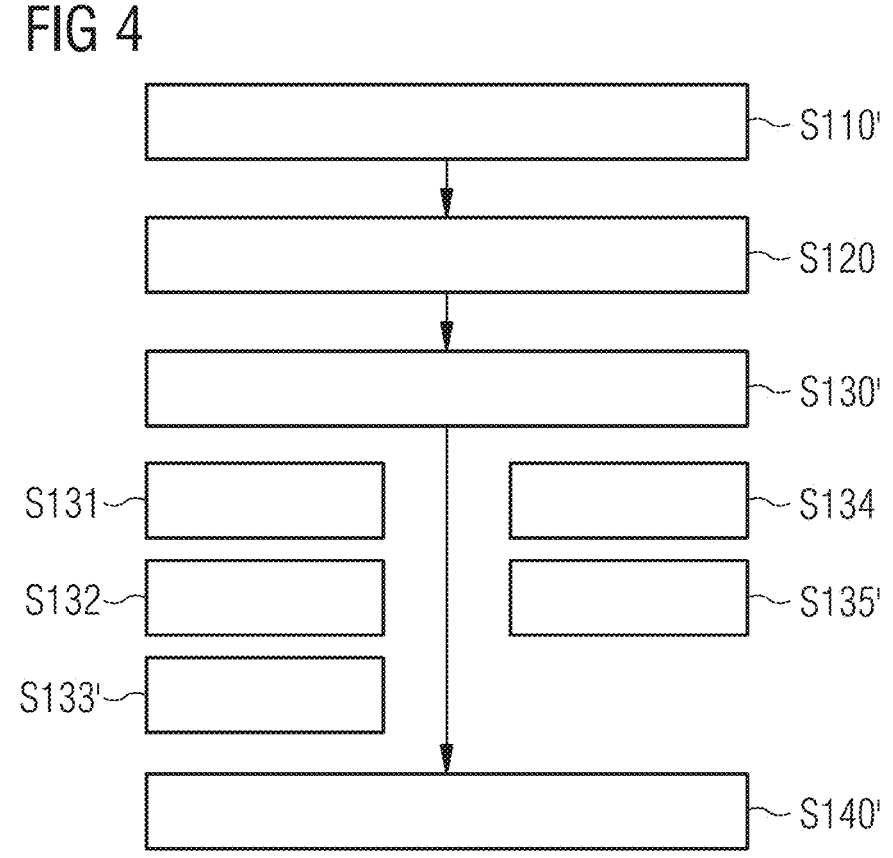
FIG. 4 depicts a flowchart illustrating a method for identifying corresponding slices of medical image data sets according to an embodiment, FIG. 5 schematically shows data streams associated with a method for identifying corresponding slices of medical image data sets according to the corresponding embodiment.
Figure 5:
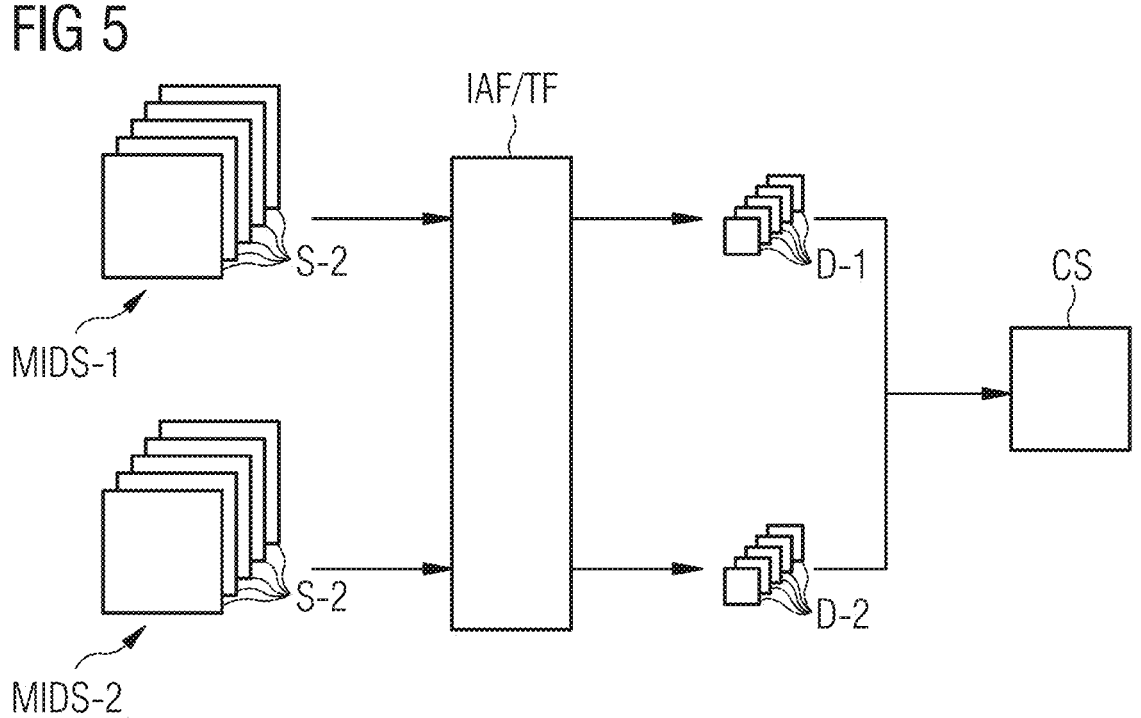

FIG. 4 depicts a method for identifying corresponding slices of medical image data sets MIDS-1, MIDS-2 according to a further embodiment of the present invention. Corresponding data streams are illustrated in FIG. 5. The method comprises several steps. The order of the steps does not necessarily correspond to the numbering of the steps but may also vary between different embodiments of the present invention. Methods steps indicated with like reference numerals as in FIG. 2 correspond to the method steps introduced and explained in connection with the embodiment of FIG. 2. Further, individual steps or a sequence of steps may be repeated.

The embodiment shown in FIGS. 4 and 5 differs from the embodiment of FIGS. 2 and 3 in that the first medical image data set MIDS-1 also relates to three-dimensional image data depicting a body part of a patient. Specifically, it as well comprises a plurality of slices S-1. According to some examples, the first and second medical image data sets MIDS-1, MIDS-2 relate to the anatomy of the same patient but have been acquired at different points in time. According to some examples, the first medical image data set MIDS-1 relates to a current image study the user is supposed to analyze and the second medical image data set MIDS-2 relates to a prior study showing the same body part but at an earlier point in time. By analyzing the first medical image data set MIDS-1 in conjunction with the second medical image data set MIDS-2, the user may thus infer how a disease progressed or if a particular treatment was successful. To assist the user in this respect, the method of FIG. 3 synchronizes the first and second medical image data sets MIDS-1, MIDS-2 in that corresponding slices CS in first and second medical image data sets MIDS-1, MIDS-2 are identified.

Step S110' of FIG. 4 corresponds to step S110 of FIG. 2 with the sole difference that the first medical image data set MIDS-1 received comprises a plurality of slices S-1. Step S120 of FIG. 4 is identical to step S120 of FIG. 2.

Step S130' of FIG. 4 differs from step S130 of FIG. 2 in that a slice correspondence CS between first and second medical image data sets is established which links distinct slices S-1 of the first medical image data set MIDS-1 to corresponding slices S-2 of the second medical image data set MIDS-2 where possible-rather than finding the one or more most similar slices S-2 to a key image KI. In other words, step S130' seeks to identify, for each slice S-1 of the first medical image data set MIDS-1, exactly one corresponding slice CS of the second medical image data set MIDS-2. Thereby, it may happen that it is not possible to find a corresponding slice CS in the second medical image data set MIDS-2 for a given slice S-1 in the first medical image data set MIDS-1 and vice versa. This may be the case, if an anatomical position of a slice S-1, S-2 comprised in one medical image data set MIDS-1, MIDS-2 is not covered by the respective other medical image data set MIDS-1, MIDS-2. In this case, according to some examples, no association of a corresponding slices is being made. The image processing of step S130' (and all optional steps) may predominantly be performed on processing system 20.

Steps S131, S132, and S134 of FIG. 2 can be adopted for the processing of FIG. 4. In particular, the same trained function TF may be used, and the second medical image data set MIDS-2 may likewise be adapted to the first medical image data set MIDS-2 by resampling the former. For instance, the second medical image data set MIDS-2 may be resampled such that the slices S-2 of the second medical image data set MIDS-2 are comparable to the slices S-1 of the first medical image data set MIDS-1 in terms of thickness, spacing, slice direction, and so forth. Self-speaking, this may also be implemented the other way round with the first medical image data set MIDS-1 being adapted to second medical data set MIDS-2.

In step S133', image descriptors D-1 are extracted from each slice S-1 of the first medical image data set MIDS-1. This can be implemented in largely the same way as explained in connection with step S134 above.

In step S135' the extracted image descriptors D-1 and D-2 are compared to identify corresponding slices CS in first and second medical image data sets MIDS-1, MIDS-2. The comparison may be carried once again by applying the similarity or distance metrics as introduced in connection with FIG. 2. The comparison may be pairwise, i.e., each slice S-1 of the first medical image data set MIDS-1 is compared with each slice S-2 of the second medical image data set MIDS-2. As an alternative, the comparison may occur in triplets where each slice is compared with two slices of the respective other medical image data set MIDS-1, MIDS-2 with the more similar slice of the two being retained for the next comparison. For each slice S-1, S-2 of a medical image data set MIDS-1, MIDS-2 exactly one or no corresponding slice CS of the respective other medical image data set MIDS-1, MIDS-2 is identified to provide an unambiguous association of slices S-1, S-2 between the two data sets MIDS-1, MIDS-2. No corresponding slice may be found, if a slice of one medical image data set MIDS-1, MIDS-2 it outside of the imaging region of the respective other medical image data set MIDS-1, MIDS-2 or if the slice-resolution of a medical image data set MIDS-1, MIDS-2 is, e.g., too coarse to provide a match for each and every slice S-1, S-2 of the medical image data set MIDS-1, MIDS-2 it is compared with (if this is not corrected in optional step S131). To make sure that the identified assignment between the slices S-1, S-2 of first and second medical image data sets MIDS-1, MIDS-2 conserves the respective slice orders and to resolve ambiguities, additional constraints or auxiliary conditions may be provided that the final result has to fulfill. Such constraints may be provided for by the order of the slices in the first and second medical image data sets MIDS-1, MIDS-2 and/or an overall degree of similarity (which should be maximized).

The result of step S130 may be conceived as an assignment which unambiguously assigns slices S-, S-2 of first and second medical image data sets MIDS-1, MIDS-2 to one another. This result may also be designated as "slice correspondence" CS. At step S140', this result may be provided to the user or subsequent processing steps. Step S140' may be performed at least partially either on user interface 10 or on processing system 20. Corresponding data exchange is included in this step where necessary.

Figure 6:
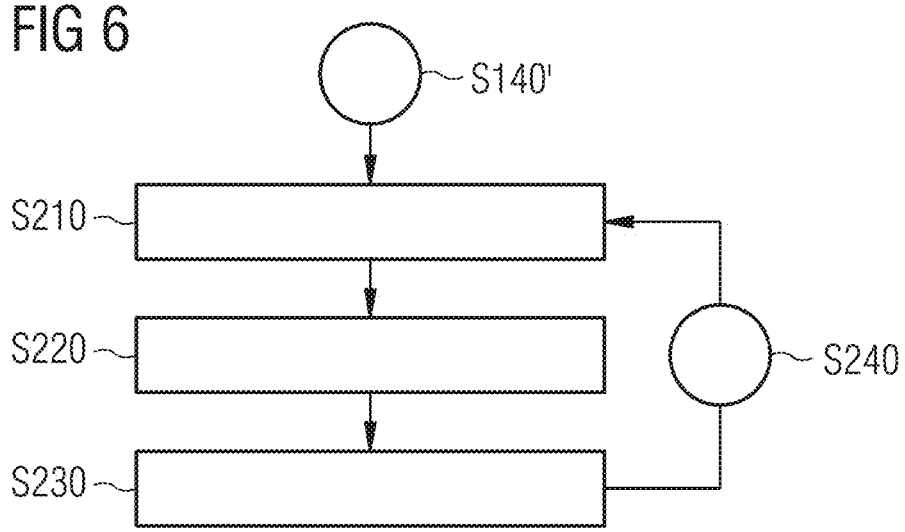
FIG. 6 depicts a flowchart illustrating further method steps based on an identification of corresponding slices of medical image data sets according to an embodiment.

FIG. 6 depicts optional methods steps that may be executed based on methods for identifying corresponding slices of medical image data sets MIDS-1, MIDS-2 according to embodiments of the present invention. In particular, the optional method steps shown in FIG. 6 may follow step S140'. The order of the steps does not necessarily correspond to the numbering of the steps but may also vary between different embodiments of the present invention. Methods steps indicated with like reference numerals as in FIG. 2 or 4 correspond to the method steps introduced and explained in connection with the embodiments of FIG. 2 or 4.

In particular, FIG. 6 illustrates how the slice correspondence CS determined in step S130' may be used to synchronize the views of two image studies. A use case for the embodiment of FIG. 6 may occur if the user has opened two image studies, i.e., first and second medical image data sets MIDS-1, MIDS-2 with the intention to compare one with the other. Here, the similar slice search introduced in connection with FIGS. 4 and 5 enables to automatically match any slice S-1 of the first medical image data set MIDS-1 with the corresponding slice S-2 of the second medical image data set MIDS-2 to the effect that if a user selects one slice, e.g., for viewing, he may be automatically provided with the respectively corresponding slice CS.

Specifically, at step S210, an input from the user is received which is indicative of a selection of a slice S-1, S-2 in either the first or second medical image data set MIDS-1, MIDS-2. The user input may, for instance, be input into the system 1 via the user interface 10. The user input may be in the form of a scrolling action while scrolling through the respective medical image data set MIDS-1, MIDS-2 in order to arrive at a desired slice S-1, S-2. For instance, such scrolling may be input using scroll wheels or jog dials or wheels, action buttons or sliders in an appropriate graphical user interfaces, gestures, voice commands or the like. Further, such user input may directly indicate the desired slice the user wants to see, e.g., by clicking on a z-axis bar indicating the z-position of the slice S-1, S-2 in the respective stack or by directly inputting the slice number. Step S210 may be performed at least partially either on user interface 10 or on processing system 20. Corresponding data exchange is included in this step where necessary.

At step S220, the respectively corresponding slice CS with respect to the slice S-1, S-2 currently selected by the user is identified. To this end, the method reverts to the slice correspondence CS determined in step S130'. Based on the slice correspondence CS, the system 1 may then calculate which slice of the respective other medical image data set MIDS-1, MIDS-2 corresponds to the slice currently selected (viewed) by the user. Step S220 may predominantly be performed on processing system 20.

At step S230, the identified corresponding slice CS is provided. "Provided" in this case may mean displaying the identified corresponding slice CS to the user in an appropriate graphical user interface. According to some examples, the identified corresponding slices CS of the synchronized medical image data sets MIDS-1, MIDS-2 may be displayed together with the currently selected one. For instance, the two slices CS, S-1 could be displayed side by side in an appropriate graphical user interface. Step S230 may be performed at least partially either on user interface 10 or on processing system 20. Corresponding data exchange is included in this step where necessary.

Step S240 is a repeat step indicating that steps S210 to S230, i.e., the receipt of a user input (S210), the identification of a thereto corresponding slice CS (S220), and the output of the corresponding slice CS (S230) may be repeated multiple times. Accordingly, the corresponding slice CS may be dynamically adapted to the slice S-1 currently selected by the user. In other words, the corresponding slice CS is updated whenever the user selects a new slice in one medical image data set MIDS-1, MIDS-2. With that, the user can simultaneously scroll through two image series. Step S240 may be performed at least partially either on user interface 10 or on processing system 20. Corresponding data exchange is included in this step where necessary.

Figure 7:
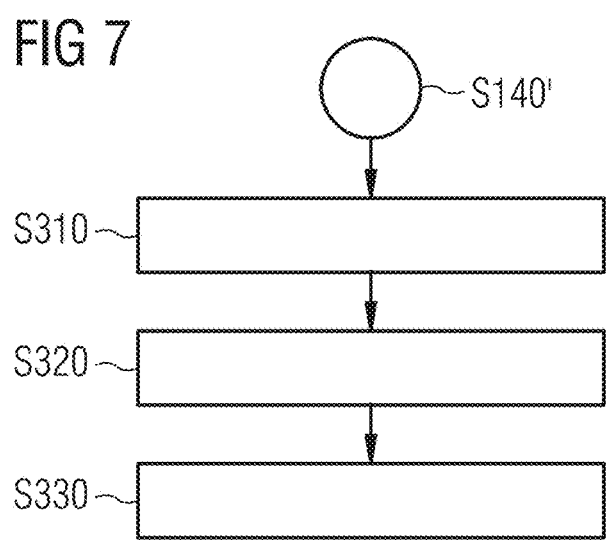
FIG. 7 depicts a flowchart illustrating further method steps based on an identification of corresponding slices of medical image data sets according to an embodiment.

FIG. 7 depicts optional methods steps that may be executed based on methods for identifying corresponding slices CS of medical image data sets MIDS-1, MIDS-2 according to embodiments of the present invention. In particular, the optional method steps shown in FIG. 6 may follow step S140'. The order of the steps does not necessarily correspond to the numbering of the steps but may also vary between different embodiments of the present invention. Methods steps indicated with like reference numerals as in FIG. 2 or 4 correspond to the method steps introduced and explained in connection with the embodiment of FIG. 2 or 4. Further, individual steps or a sequence of steps may be repeated.

In particular, FIG. 7 illustrates how the similar slice search explained in connection with FIG. 4 can be used to infer whether or not two medical image data sets MIDS-1, MIDS-2 are comparable and therefore suited for comparative reading by a user. Specifically, the slice correspondence CS is used to determine an overlap of the imaging volumes of first and second medical image data sets MIDS-1, MIDS-2. The higher this overlap the better can the two medical image data sets MIDS-1, MIDS-2 allegedly be compared.

Accordingly, step S310 is directed to determine, based on the slice correspondence CS provided in step S140', an anatomic overlap of the corresponding medical image data sets MIDS-1, MIDS-2. The anatomic overlap may be determined from the number of slices respectively corresponding to one another in first and second medical image data sets MIDS-1, MIDS-2. According to further examples, the anatomic overlap may be determined from those corresponding image pairs marking the end of the overlapping area of first and second medical image data sets MIDS-1, MIDS-2. The anatomic overlap may be measured in arbitrary units along the stacking direction of the slices S-1, S-2 in first and second medical image data sets MIDS-1, MIDS-2. Step S310 may predominantly be performed on processing system 20.

At step S320, a degree of comparability for first and second medical image data sets MIDS-1, MIDS-2 is calculated based on the anatomic overlap. According to some examples, the degree of comparability may be the anatomic overlap as such. According to further examples, additional information may be factored in. Such additional information may, for instance, be the time span between first and second medical image data sets MIDS-1, MIDS-2 have been acquired (the more time has elapsed the less comparable two image series may be), the type of the respective image modality used for acquiring the medical image data sets MIDS-1, MIDS-2 (data acquired with like modalities may be more comparable), meta-data comprised in first and/or second medical image data sets MIDS-1, MIDS-2 and so forth. Step S320 may predominantly be performed on processing system 20.

At step S330, the degree of comparability is provided. "Provided" may mean that the determined degree of comparability is brought to the attention of the user. If two image series are difficult to compare, the user may thus receive a warning message and maybe select another one for comparative reading. Further, "provided" may mean that the degree of comparability is put on record for the two medical image data sets MIDS-1, MIDS-2, i.e., stored in the medical information system 50 for later use. Step S330 may be performed at least partially either on user interface 10 or on processing system 20. Corresponding data exchange is included in this step where necessary.

Figure 8:
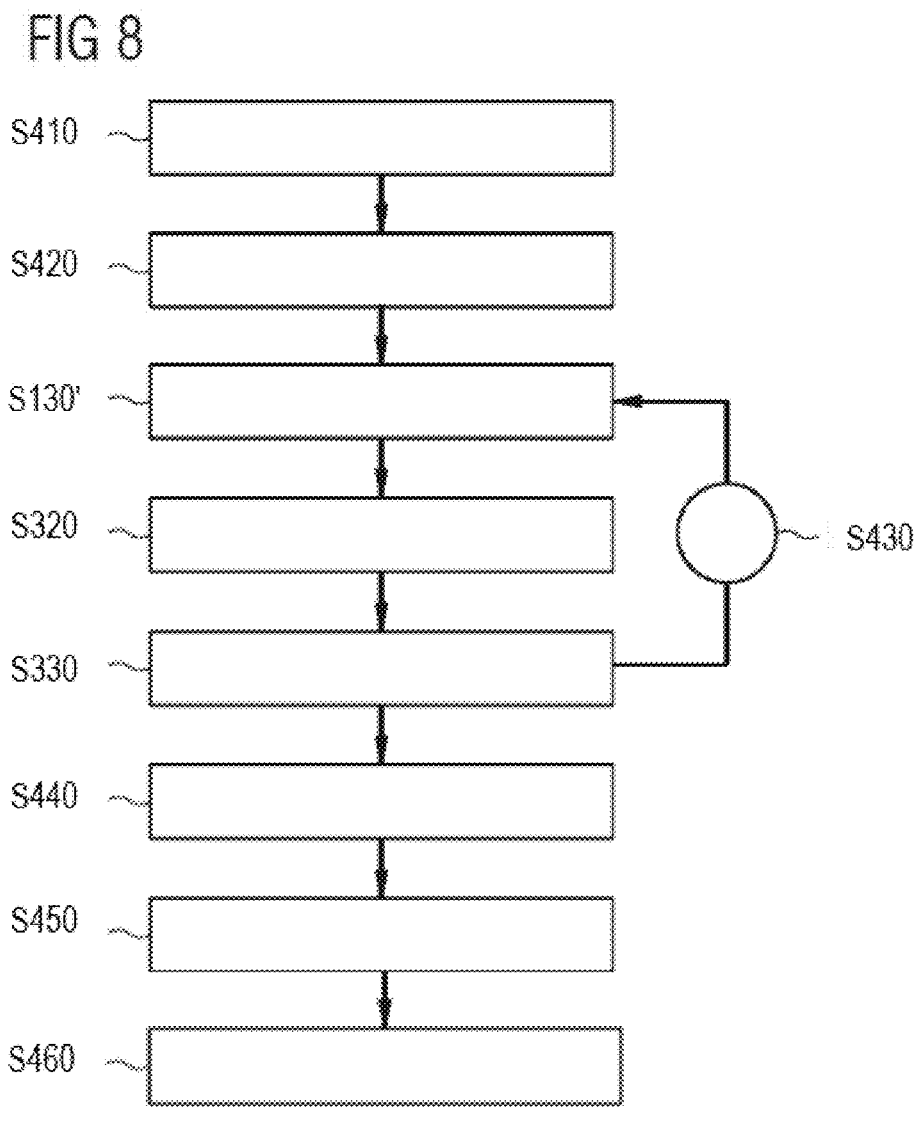
FIG. 8 depicts a flowchart illustrating a method for selecting one or more medical image data sets according to an embodiment.

FIG. 8 depicts a method for determining a degree of comparability of medical image data sets MIDS-1, MIDS-2. The method comprises several steps. The order of the steps does not necessarily correspond to the numbering of the steps but may also vary between different embodiments of the present invention. Methods steps indicated with like reference numerals as in FIGS. 2, 4, and/or 7 correspond to the method steps introduced and explained in connection with the respective embodiments. Further, individual steps or a sequence of steps may be repeated.

Figure 9:
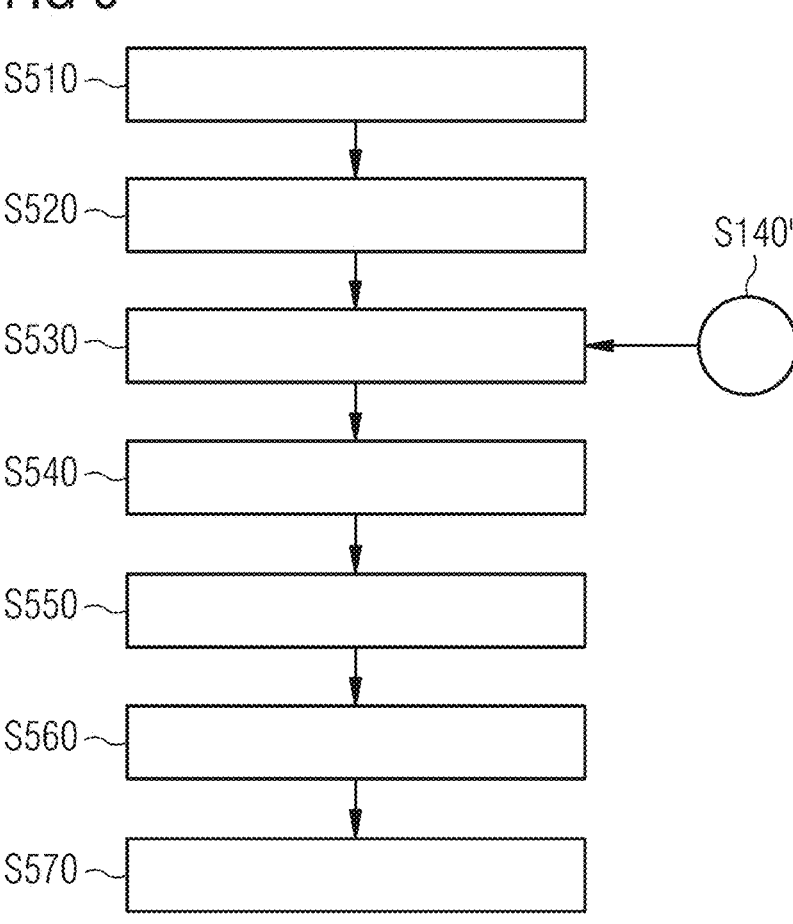
FIG. 9 depicts a flowchart illustrating a method based on an identification of corresponding slices of medical image data sets according to an embodiment.

The embodiment shown in FIGS. 8 and 9 builds on the above embodiments to provide a method capable of automatically evaluating and/or selecting medical image data sets MIDS-1, MIDS-2 for comparative reading from a plurality of data sets coming into question.

A first step S410 is directed to receive a first medical image data set MIDS-1. The first medical image data set MIDS-1 may be conceived as the current study of a patient which the user is about to read. Apart from that, step S410 corresponds to step S110'.

Step S420 is directed to retrieve a plurality of second medical image data sets MIDS-2 which come into question for comparative reading in conjunction with the first medical image data set MIDS-1. In other words, the second medical image data sets MIDS-2, in this case, may relate to prior studies of the patient which have been taken at an earlier point in time than the first medical image data set MIDS-1 (making the first medical image data set MIDS-1 the "follow-up study" in this case). To this end, the system 1 may query medical information system 50 for appropriate second medical image studies MIDS-2. For instance, an appropriate case or patient identifier such as the patient name or ID may be extracted from the first medical image data set MIDS-1 and used as a search term. Step S110 may be performed at least partially either on user interface 10 or on processing system 20 or on medical information system 50. Corresponding data exchange is included in this step where necessary.

That followed, for each of the retrieved second medical image data sets MIDS-2, the steps S130', S320, and S330 are repeated via repeat step S430. These steps may predominantly be performed on processing system 20. As before, step S130' identifies the slice correspondence CS between the first medical image data set MIDS-1 and the respective second medical image data set MIDS-2. Thereby, step S130' may, in particular, comprise sub-steps S131, S134 and/or S135 which would be repeated for each second medical image data set MIDS-2. Other optional sub-steps of step S130' which are not related to the second medical image data sets MIDS-2, such as steps S132 and/or S133 are preferably not repeated for every second medical image data set MIDS-2 but carried out only once in the method of FIG. 8. Steps S320 and S330 are identical to the steps shown in connection with FIG. 7 and yield a degree of comparability for each second medical image data set MIDS-2 indication a comparability of the respective second medical image data set MIDS-2 with the first medical image data set MIDS-1.

In step S440, the degrees of comparability are provided to the user or for further processing. For instance, the degrees of comparability may be displayed to the user in conjunction with the respective second medical image data set MIDS-2. With that, the user may be provided with a quick overview which of the available second medial image data sets MIDS-2 is suited for follow-up reading. Accordingly, the user is brought into a position where he may purposefully select appropriate second medial image data sets MIDS-2. Step S440 may be performed at least partially either on user interface 10 or on processing system 20. Corresponding data exchange is included in this step where necessary.

Further, the degree of comparability may be used to automatically select or pre-select appropriate second medical image data sets MIDs-2 in step S450. For instance, the system 1 may select all second medical image data sets MIDS-2 the degree of comparability (the anatomical overlap) of which is greater than a predetermined threshold. The thus selected second medical image data sets MIDS-2 may then be provided in step S460. Thereby, "provided" may mean presenting them to the user via user interface 10 for review and further selection and/or loading them in a temporary memory of the system 1. Step S110 may be performed at least partially either on user interface 10 or on processing system 20 or on medical information system 50. Corresponding data exchange is included in this step where necessary.

FIG. 9 depicts optional method steps for determining a temporal evolution of one or more lesions using the similar slice search according to one or more of the above embodiments. The method comprises several steps. The order of the steps does not necessarily correspond to the numbering of the steps but may also vary between different embodiments of the present invention. Methods steps indicated with like reference numerals as in FIGS. 2 and/or 4 correspond to the method steps introduced and explained in connection with the respective embodiments. Further, individual steps or a sequence of steps may be repeated.

Step S510 is directed to identify, in the first medical image data set MIDS-1, one or more relevance slices. Relevance slices are characterized in that they depict one or more lesions of a body part of a patient such as lesions in the lung or liver tissue of a patient. In addition to that or as an alternative, relevance slices may be characterized in that they comprise one or more previous annotations of a user which may, for instance, point at the presence of one or more lesions in that slice. Relevance slices may, for instance, be identified by applying an appropriate computer aided detection algorithm configured to detect lesions in medical image data. Step S510 may predominantly be performed on processing system 20.

Step S520 is directed to detect one or more lesions in the one or more relevance slices, e.g., by using said computer-aided detection algorithms. Step S520 may be comprised in step S510 if the relevance slices have been identified by detecting slices having lesions in the first place. Step S520 may predominantly be performed on processing system 20.

At step S530 corresponding slices are identified in the second medical image data set MIDS-2, which corresponding slices correspond to the relevance slices. The identification of the corresponding slices in the second medical image data set MIDS-2 is effected on the basis of the slice correspondence CS calculated in step S130' and provided in step S140' of FIG. 4. Step S530 may predominantly be performed on processing system 20.

At step S540, one or more corresponding lesions are detected in the corresponding slices identified in step S530. This again can be done by applying a computer-aided detection algorithm to the image data of the corresponding slices. Step S540 may predominantly be performed on processing system 20.

At step S550, the lesions detected in the first medical image data set MIDS-1 are matched with the corresponding lesions. In other words, the lesion of the first medical image data set MIDS-1 are unambiguously assigned to corresponding lesions so that pairs of a lesion and a corresponding lesion result. Lesions that cannot be assigned in that way remain unpaired and designate new or vanished lesions, as the case may be. Such new or vanished lesions may optionally brought to the attention to the user, e.g., by outputting an appropriate marking in the image data displayed in a graphical user interface. Lesions may be matched by evaluating their position in the respective slices, their relative position to one another or with respect to other anatomical structures, their shape, their properties (such as degree of calcification, structure at the boundary, etc.), size, optical properties and so forth. For matching the lesions in step S550, designated computer aided lesion matching algorithms may be applied. Step S550 may predominantly be performed on processing system 20.

Step S560 is directed to determine a temporal evolution of one or more of the lesions detected in first and second medical image data sets MIDS-1, MIDS-2 based on the matching of step S550. To this end, one or more measurement values may be extracted for each lesion and compared to the matching lesion. For instance, such measurement values may relate to geometric values such as the size, diameter, volume of the lesions and so forth. A temporal evolution results which shows the how a particular lesion progressed. Further, average values/temporal evolutions for a variety of lesion pairs may be calculated. Step S560 may predominantly be performed on processing system 20.

At step S570, the temporal evolution(s) thus determined is/are provided. Specifically, the temporal evolutions may be provided to a user, e.g., in the form of a trending, graph or as a pop-up window which opens when the user hovers over a lesion (e.g., with a mouse cursor). Further, the temporal evolutions may be provided by associating them to the individual lesions. In addition to that or as an alternative, the temporal evolutions may be provided, i.e., included, to a structured medical report to be archived in the medical information system 50. Step S110 may be performed at least partially either on user interface 10 or on processing system 20. Corresponding data exchange is included in this step where necessary.

Self-speaking, the above is not only applicable to two medical image data sets with the temporal evolution(s) then indicating a progression of individual lesions over more than two points in time. Further, the automated extraction of a temporal evolution for one or more lesions is compatible with the automated selection of the right priors for follow-up reading according to the foregoing embodiment. Specifically, it can be conceived that, firstly, one or more second medical image data sets MIDS-2 are determined which have a sufficient anatomical overlap with the first medical image data set MIDS-1 and then, secondly, a temporal evolution of the lesions comprised the first medical image data set MIDS-1 and the thus identified second medical image data set(s) MIDS-2 is inferred.

As already detailed above in connection with the other embodiments, the processing steps for identifying corresponding slices in medical image data sets MIDS-1, MIDS-2 may be carried out by a trained function TF configured to determine a similarity between two-dimensional medical images.

Generally, such trained functions TF may relate to intelligent agents or classifiers suited for classifying image data according to a learned task. They may relate to any type of method or apparatus capable of predicting to what extent the image data of a pair of two-dimensional medical images is similar. This definition comprises, but is not limited to, data mining tools and techniques such as Support Vector Machines, decision trees, naive Bayes or (convolutional) neural networks. Specifically, according to an implementation, the trained function TF may comprise a convolutional neural network. In an embodiment, the arrangement of the trained function TF is a fully convolutional neural network. Alternative network arrangements may be used, for example, a 3D Very Deep Convolutional Network (3D-VGGNet), wherein a VGGNet stacks many layer blocks containing narrow convolutional layers followed by max pooling layers.

A convolutional neural network is defined in the form of a plurality of sequential layers. The term sequential is used to indicate the general flow of output feature values from one layer to input to a next layer. The information from the next layer is fed to a next layer, and so on until the final output layer. Layers may only feed forward or may be bi-directional, including some feedback to a previous layer. The layers may be weighted. Further, each layer generally comprises a number of nodes that are also weighted. Essentially, each node can be seen as executing a mathematical operation mapping one or more input values to an output value. The nodes of each layer may connect with all or only a sub-set of nodes of a previous and/or subsequent layer. Two nodes are "connected" if their inputs and/or outputs are connected. Input values for the nodes of the input layer are image element values, preferably pixel values, of the respective images KI or slices S-1, S-2. The last layer is the output layer outputting a degree of similarity between the input image data. The output may be in the form of a continuously varying value indicative of the degree of similarity. According to other examples, the output (the degree of similarity) may take a binary form indicating whether or not two images are similar. In between input and output layer, there is a number of hidden layers. A first group of neural network layers may be applied to extract features from images. In this case, medical images, i.e. the gray scale and/or color values for each individual image element of the image, serve as input values for the neural network. The thus extracted features like, contrast, gradients, texture, density, or the like may be fed as input values to a second group of network layers, also known as classifiers, which serve to further assign objects and/or characteristics to at least one of the extracted features present in the image. Various types of layers may be used, such as convolutional, pooling (e.g., max-pooling or average-pooling), up-sampling, deconvolutional, fully connected, or other types of layers. Convolutional layers convolve the input and pass its result to the next layer by moving an image filter kernel over the input. Pooling layers reduce the dimensions of the data by combining the outputs of node clusters at one layer into a single node in the next layer, thereby streamlining the underlying computation. Up-sampling and deconvolution layers reverse the actions of convolution and pooling layer in terms of the abstraction level. A fully connected layer connects every node in one layer to every node in another layer, so that essentially every feature gets a "vote". According to an implementation, skip connections may by used, so that layers may also output to other layers than the sequentially next layer introducing one or more residual blocks or layers. Such configuration is also referred to as ResNet. Using residual blocks results in the ability to train much deeper networks as this alleviates the vanishing gradient problem known from very deep neural networks.

According to some examples, the trained function TF may be configured to carry out the task of extracting image descriptors from two-dimensional images (also referred to as encoding) and the task of evaluating the similarity between two images (i.e., determining a degree of similarity) by comparing image descriptors of these images (also referred to as decoding). Accordingly, the trained function may comprise at least an encoder branch and a decoder branch.

According to some examples, the trained function may include multiple encoder branches and a decoder branch. Each encoder branch may process a two-dimensional image to extract an image descriptor D-1, D-2 therefrom. The decoder branch processes a merged latent image descriptor data structure that is obtained from aggregating image descriptors D-1, D-2 that are obtained from the encoder branches. The multiple encoder branches processing the two-dimensional images are copies of each other that share the same parameters. The encoder branches can include convolutional layers. As a general rule, any CNN backbone like ResNet or a custom design can be used. The weights of the encoder branches may be shared between the encoder branches, enabling efficient learning and processing of each layer of the network. This means that the multiple encoder branches processing the individual two-dimensional images can share the same parameters, i.e., the same weights can be used for all encoder branches. This can be enforced during the training, by changing the weights in a shared manner. Sometimes, a concept of sharing parameters between multiple encoder branches is referred to as Siamese copies. Specifically, a network comprising two encoder branches may be referred to as Siamese network, while a network comprising three encoder branches may be referred to as triplet network. The encoder branches may be configured such that the image descriptors D-1, D-2 of dissimilar image pairs are pushed further apart in the features space of the image descriptors than the image descriptors D-1, D-2 of similar image pairs.

Processing the image descriptors D-1, D-2 in the decoding branch may mean that a learned or preset distance or similarity metric is applied to evaluate the similarity between two image descriptors D-1, D-2. The similarity metric may be configured such that a distance of two image descriptors D-1, D-2 is appropriately quantified in the feature space of the image descriptors D-1, D-2. The distance or similarity metric may take the form of mathematical functions by, e.g., outputting the cosine-similarity or the L1-norm for the respective image descriptors D-1, D-2. Further, the similarity metric may be embodied by one or more network layers with appropriately adapted weights or parameters.

Generally, the trained function TF of this embodiment learns by adapting weights or weighting parameters of individual layers and nodes based on training data. Rather than pre-programming potential signs of similar medical images, the architecture of the trained function TF is defined to learn these patterns at different levels of abstraction based on input data. Trained function TF may preferably be trained using a method according to supervised learning. Well established is the backpropagation method, which may be applied for embodiments of the present invention. During training, trained function TF is applied to training input values to produce corresponding output values the target values of which are known. The difference between produced and target output values (e.g., in the form of the mean squared error (MSE) of the difference between produced and target values) may be used to introduce a cost or loss function as a measure of how good or bad trained function TF performs. The goal of the training is to find a (local) minimum of the loss function by iteratively adjusting the weights of trained function TF so that trained function is finally enabled to generate acceptable results across a (suf-ficiently) large cohort of training data. This optimization problem can be carried out using stochastic gradient descent or other approaches known in the art.

In principle, a trained function TF comprising one or more encoder branches and a decoder branch can be trained by adapting either the encoding (i.e., the extraction of image descriptors) or the decoding (i.e., the quantification of the image similarities) or both. For instance, the one or more encoder branches can be adapted such that particularly meaningful image descriptors D-1, D-2 are extracted. Fur-ther, the decoder branch may be trained such that an appro-priate similarity metric is learned and/or applied.

According to some examples, the loss function may comprise a triplet loss function. Triplet loss is a loss function where a baseline (anchor) input is compared to a positive (similar) input and a negative (dissimilar) input. The dis-tance from the baseline (anchor) input to the positive input is minimized, and the distance from the baseline input to the negative input is maximized.

According to an embodiment, a general training scheme may take the following form. Firstly, a trained function TF is received. The trained function may already be pre-trained or not having been trained at all. Next, a training data set may be provided, which comprises a plurality of images and predetermined degrees of similarity indicating a similarity between the images comprised in the training image data set. In particular, the images comprised in the training image data set may have been extracted from medical image data sets MIDS-1, MIDS-2 of one or more patients. The images comprised in the training image data set may then be inputted into the trained function TF in order to determine, by the trained function TF, degrees of similarity respectively indicative of a similarity between image pairs of the training image data set. The thus determined degrees of similarity may then be compared with the predetermined degrees of similarity. Finally, based on this comparison, the trained function TF may be adjusted and the thus adjusted trained function TF may be provided for further training or deploy-ment.

Figure 10:
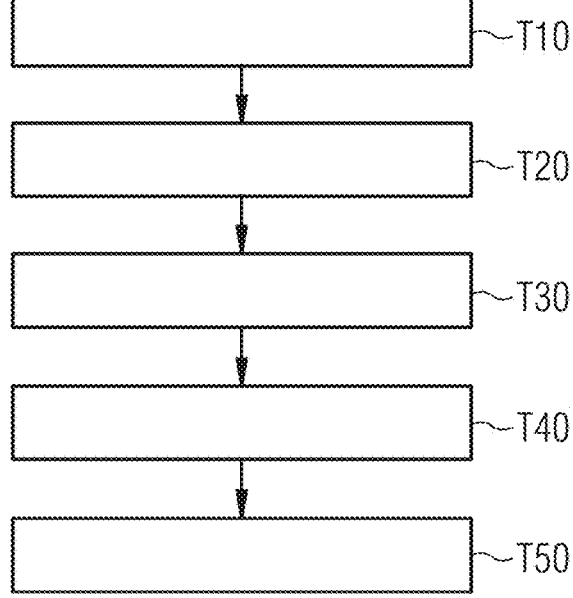
FIG. 10 depicts a flowchart illustrating a method for training trained functions to identify corresponding slices of medical image data sets according to an embodiment.

In addition to that or as an alternative, FIG. 10 depicts specific method steps for training a trained function TF to determine a similarity between two-dimensional medical images. The order of the steps does not necessarily corre-spond to the numbering of the steps but may also vary between different embodiments of the present invention.

A first step T10 is directed to receive a trained function TF, which may be pre-trained or not having been trained before. The trained function TF may be received from a memory (e.g., in the form of a library of KI models) and stored in a temporary memory.

A subsequent step T20 is directed to provide a training image data set at least comprising three two-dimensional medical images. The two-dimensional medical images have been extracted from one or more medical image data sets MIDS-1, MIDS-2 respectively depicting image volumes of body parts of patients. The medical images are preferably of the same type as the slices S-1, S-2 or key images KI to be processed by the deployed and readily trained trained func-tion TF. Accordingly, the medical images each likewise show a section of body part of a patient, may depict a plurality of anatomic structures and organs, and have been acquired using one of the abovementioned medical imaging modalities. According to some implementations, first and second medical image data sets MIDS-1, MIDS-2 as intro-duced above may be used in this regard. According to some examples, the two-dimensional medical images have been extracted from the same medical image study. The two-dimensional images are characterized in that (are chosen such that) the second medical image has a greater similarity to the first medical image than the third medical image has to the first medical image. In other words, the first medical image can be conceived as an anchor while the second medical image is the positive image and the third medical image is the negative image.

In subsequent step T30, the first, second and third medical images are input into the trained function TF, which, at step T40 determines a first degree of similarity between the first medical image and the second medical image and a second degree of similarity between the first medical image and the third medical image. Specifically, the trained function TF may extract image descriptors D-1, D-2 from first, second and third medical images, respectively. In other words, the trained function TF may encode first, second, and third medical images, respectively. That followed, the trained function may infer first and second degrees of similarities by comparing the respectively extracted image descriptors. In this regard, the trained function TF may apply a similarity metric capable of outputting a distance of the respective image descriptors in the encoding space.

Next, at subsequent step T50, the trained function TF is adjusted such that the first degree of similarity is greater than the second degree of similarity. This adjustment may amount to adapt the encoding, i.e., the process of image descriptor extraction, and/or the decoding, i.e., the process of applying an appropriate similarity metric. According to some examples however, the similarity metric may also be held fixed as, e.g., the Euclidian distance or the cosine similarity. In that case, any adaptation of the trained function would focus on the encoding branch or branches.

Figure 11:
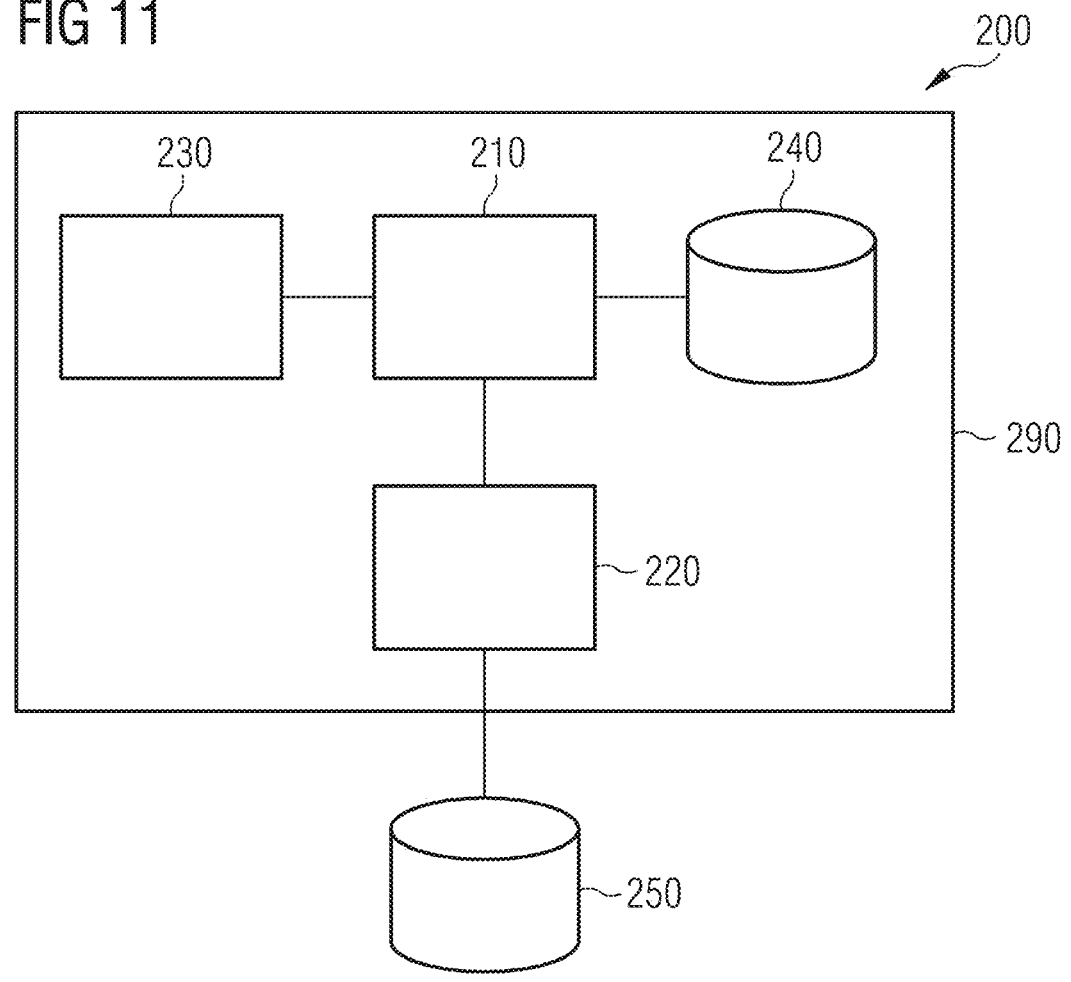
FIG. 11 shows a system for training trained functions to identify corresponding slices of medical image data sets according to an embodiment.

FIG. 11 illustrates an embodiment of a system 200 for training trained function TF. The system comprises a pro-cessor 210, an interface 220, a memory 230, a storage 240, and a database 250. Processor 210, interface 220, memory 230 and storage 240 may be embodied by a computer 290. Processor 210 controls the overall operation of the computer 200 by executing computer program instructions which define such operation. The computer program instructions may be stored in memory 230 or in storage 240 and loaded into memory 230 when execution of the computer program instructions is desired. Storage 240 may be a local storage as a component of the system 200, or a remote storage acces-sible over a network, such as a component of a server or cloud system. The method steps illustrated in FIG. 10 may be defined by the computer program instructions stored in memory 230 and/or storage 240, and controlled by processor 210 executing the computer program instructions.

Database 250 is a storage device such a cloud or local storage serving as an archive for the training data sets comprising first, second, and third medical images as intro-duced above. Database 250 may be connected to computer 290 for receipt of one or more medical images. It is also possible to implement database 250 and computer 290 as a single device. It is further possible that database 250 and computer 290 communicate wirelessly or with wired con-nection through a network. Interface 220 is configured to interact with database 250.

It will be understood that, although the terms first, second, etc. may be used herein to describe various elements, components, regions, layers, and/or sections, these elements, components, regions, layers, and/or sections, should not be limited by these terms. These terms are only used to distin-guish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concur-rently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representa-tions of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed seri-ally in two consecutive blocks may actually be performed simultaneously, or in some cases be performed in reverse order. Although the flowcharts describe the operations as sequential processes, many of the operations may be per-formed in parallel, concurrently or simultaneously. In addi-tion, the order of operations may be re-arranged. The pro-cesses may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodi-ments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined man-ner. Portions of the example embodiments and correspond-ing detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requir-ing physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The following points are also part of the disclosure:

1. Computer-implemented method for identifying corresponding slices of medical image data sets (MIDS-1, MIDS-2), the method comprising the following steps:
   receiving (S100, S100') a first medical image data set (MIDS-1);
   receiving (S110) a second medical image data set (MIDS-2) different from the first medical image data set (MIDS-1);
   providing (S121) a trained function (TF) configured to determine a similarity between two-dimensional medical images;
   identifying (S120, S120'), from a plurality of slices (S-2) comprised in the second medical image data set (MIDS-2), at least one corresponding slice corresponding to image data comprised in the first medical image data set (MIDS-1) by evaluating similarities between the first and second medical image data sets (MIDS-1, MIDS-2) using the trained function.

2. Method according to point 1, wherein
   the first medical image data set (MIDS-1) comprises a plurality of slices (S-1); and
   the step of identifying the at least one corresponding slice comprises:
   identifying (S120') for each of a plurality of slices (S-1) of the first medical image data set (MIDS-1) one corresponding slice of the second medical image data set (MIDS-2) by evaluating similarities between the first and second medical image data sets (MIDS-1, MIDS-2) using the trained function (TF) so as to provide a slice correspondence (CS) between the first and second medical image data sets (MIDS-1, MIDS-2).

3. Method according to point 2, further with the steps:
   determining (S320) an anatomical overlap between the image volume of first medical image data set (MIDS-1) and the image volume of the respective second medical image data set (MIDS-2) based on the identified slice correspondence (CS);
   evaluating (S330) a degree of comparability of the second medical image data set (MIDS-2) with the first medical image data set (MIDS-1) based on the determined anatomical overlap;
   providing the degree of comparability to a user via a user interface.

4. Method according to points 2 or 3, further with the steps of
   receiving (S210) an input from a user indicative of a selection of a slice of the first medical image data set (MIDS-1) in order to designate a selected slice;
   identifying (S220), from the plurality of slices (S-2) of the second medical image data set (MIDS-2), the slice corresponding to the selected slice based on the identified slice correspondence (CS); and
   providing the slice (CS) corresponding to the selected slice.

5. Method according to any of points 2 to 4, wherein
   in the step of identifying (S120') for each of a plurality of slices (S-1) of the first medical image data set (MIDS-1) one corresponding slice of the second medical image data set (MIDS-2) one or more of the following constraints are additionally being used:
   an overall degree of similarity is maximized, the overall degree of similarity being a measure for the cumulative similarity of individual slice pairs of first and second medical image data sets (MIDS-1, MIDS-2); and/or
   slice order of first and/or second medical image data sets (MIDS-1, MIDS-2) is retained.

6. Method according to any of the preceding points, wherein the trained function (TF) is further configured to respectively extract image descriptors (D-1, D-2) from two-dimensional medical images and determine the similarity between two-medical medical images based on the extracted image descriptors (D-1, D-2), wherein the method comprises:
   extracting (S122) at least an image descriptor (D-1) from the first medical image data set (MIDS-1) by the trained function (TF);
   extracting (S123) an image descriptor (D-2) from each of a plurality of slices (S-2) of the second medical image data set MIDS-2) by the trained function (TF);
   wherein the at least one corresponding slice is identified (S120') based on the extracted image descriptors (D-1, D-2) by the trained function (TF).

7. Method according to point 6, wherein the first medical image data set (MIDS-1) comprises a plurality of slices (S-1) and the method further comprises the step of:
   extracting (S122') an image descriptor (D-1) from each of a plurality of slices (S-1) of the first medical image data set (MIDS-1).

8. Method according to any of the preceding points, wherein
   the first and second medical image data sets (MIDS-1, MIDS-2) at least partially depict the same body part either
   of the same patient at different points in time, or
   of different patients.

9. Method according to any of the preceding points, wherein:
   first and second medical image data sets (MIDS-1, MIDS-2) respectively comprise magnetic resonance image data;
   the first medical image data set (MIDS-1) has been acquired using a first magnetic resonance imaging protocol; and
   the second medical image data set has been acquired using a second magnetic resonance imaging protocol different to the first magnetic resonance imaging protocol.

10. Method according to any of the preceding points, wherein:
    the first medical image data set has been acquired using a first medical imaging modality;

the second medical image data set has been acquired using a second medical imaging modality; and the first medical imaging modality is based on an imaging technology different from the imaging technology the second modality is based on, the first modality being preferably based on an x-ray imaging technology and the second medical image data set being preferably based on a magnetic resonance imaging technology.

11. Method according to any of the preceding points, wherein:

the first medical image data set comprises a two-dimensional key image indicative of at least one finding previously reported for a patient; and the second medical image data set comprises an image study the reference image has been extracted from upon reporting the at least one finding for the patient.

12. Method according to any of the preceding points further comprising resampling the second medical data set based on the first medical image data set in order to define a plurality of slices in the second medical image data set.

13. Method according to any of the preceding points, wherein the trained function applies a learned metric to determine the similarity between two-dimensional medical images, the trained function preferably comprising a deep metric learning network.

14. Method according to any of the preceding points, wherein the trained function comprises a Siamese network and/or a triplet network.

15. Method according to any of the preceding points, wherein the trained function has been trained using a triplet loss function or a contrasting loss function.

16. Method according to any of the preceding points wherein the trained function is configured to determine similarities between two-dimensional medical images by:

comparing a first candidate image to a reference image and comparing a second candidate image to the reference image, the reference image being extracted from one of the first and second medical image data sets and the first and second candidate images being extracted from the respective other one of the first and second medical image data set; and determining which one of the first and second candidate images has a higher degree of similarity to the reference image.

17. Computer-implemented method for identifying corresponding slices in medical image data sets, the method comprising the following steps:

providing a trained function configured to determine a similarity between two-dimensional medical images;

receiving a two-dimensional key image indicative of at least one finding previously reported for a patient;

retrieving a first medical image data set corresponding to the reference image;

identifying, from a plurality of slices of the first medical image data set, at least one corresponding slice with respect to the key image by evaluating similarities between the key image and the first medical image data set using the trained function so as to provide a first assignment between the key image and a corresponding slice in the first medical image data set;

receiving a second medical image data set, the second medical image data set at least partially depicting the same body part of the patient as the first medical image data set but having been acquired at a different point in time than the first medical image data set;

identifying, for each of a plurality of slices of the first medical image data set one corresponding slice of a plurality of slices of the second medical image data set by evaluating similarities between the first and second medical image data sets using the trained function so as to provide a second assignment between slices of the first medical image data set and slices of the second medical image data set;

selecting at least one slice from the second medical image data set based on the first assignment and on the second assignment so as to provide a selected slice, the selected slice having a certain degree of similarity to the key image.

18. Computer-implemented method for determining a degree of comparability of medical image data sets;

receiving a first medical image data set;

receiving a plurality of second medical image data sets, first and second medical image data sets having been acquired from the same patient at different points in time, respectively;

providing a trained function configured to determine a similarity between two-dimensional medical images;

for each second medical image data set:

identifying those slices having a corresponding slice in the first medical image data set as overlapping slices by evaluating similarities between the first and second medical image data sets using the trained function; and determining an anatomical overlap between the image volume of first medical image data set and the image volume of the respective second medical image data set based on the overlapping slices;

determining a degree of comparability for each of the second medical image data sets with the first medical image data set based on the determined anatomical overlaps.

19. Computer-implemented method for providing a trained function comprising the following steps:

receiving a trained function;

providing a first two-dimensional medical image, a second two-dimensional medical image, and a third two-dimensional medical image, wherein:

first second and third medical images have been extracted from one or more medical image studies respectively depicting image volumes of body parts of patients; and the second medical image has a greater similarity to the first medical image than the third medical image has to the first medical image;

inputting the first, second and third medical images into the trained function;

determine a first degree of similarity between the first medical image and the second medical image and a second degree of similarity between the first medical image and the third medical image;

adjusting the trained function such that the first degree of similarity is greater than the second degree of similarity; and providing the trained function.

20. System for identifying corresponding slices of medical image data sets, the system comprising:

an interface for receiving a first medical image data set and a second medical image data set different from the first medical image data set; and

US 12,579,648 B2

51 a computing unit configured to run a trained function configured to determine a similarity between two-dimensional medical images;

the computing unit being further configured to:

identify, from a plurality of slices comprised in the second medical image data set, at least one corresponding slice corresponding to image data comprised in the first medical image data set by evaluating similarities between the first and second medical image data sets using the trained function.

21. System for determining a degree of comparability of medical image data sets, the system comprising:

an interface for receiving a first medical image data set and a plurality of second medical image data set different from the first medical image data set, first and second medical image data sets having been acquired from the same patient at different points in time, respectively; and a computing unit configured to run a trained function configured to determine a similarity between two-dimensional medical images;

the computing unit further being configured to:

for each second medical image data set:

identify those slices having a corresponding slice in the first medical image data set as corresponding slices by evaluating similarities between the first and second medical image data sets using the trained function; and determine an anatomical overlap between the image volume of first medical image data set and the image volume of the respective second medical image data set based on the corresponding slices;

determine a degree of comparability for each of the second medical image data sets with the first medical image data set based on the determined anatomical overlaps.

22. System for identifying corresponding slices in medical image data sets, the system comprising:

an interface for receiving a two-dimensional key image indicative of at least one finding previously reported for a patient, retrieving a first medical image data set corresponding to the reference image, and a and a second medical image data set, the second medical image data set at least partially depicting the same body part of the patient as the first medical image data set but having been acquired at a different point in time than the first medical image data set; and a computing unit configured to run a trained function configured to determine a similarity between two-dimensional medical images;

the computing unit further being configured to:

retrieving the first medical image data set based on the reference image via the interface;

identify, from a plurality of slices of the first medical image data set, at least one corresponding slice with respect to the key image by evaluating similarities between the key image and the first medical image data set using the trained function so as to provide a first assignment between the key image and a corresponding slice in the first medical image data set;

identify, for each of a plurality of slices of the first medical image data set, one corresponding slice of a plurality of slices of the second medical image data set by evaluating similarities between the first and second medical image data sets using the trained function so as to provide a second assignment between slices of the first medical image data set and slices of the second medical image data set;

select at least one slice from the second medical image data set based on the first assignment and on the second assignment so as to provide a selected slice, the selected slice having a certain degree of similarity to the key image.

23. System for providing a trained function configured to determine a similarity between two-dimensional medical images, the system comprising:

an interface for receiving a trained function, a first two-dimensional medical image, a second two-dimensional medical image, and a third two-dimensional medical image, wherein:

first second and third medical images have been extracted from one or more medical image studies respectively depicting image volumes of body parts of patients; and the second medical image has a greater similarity to the first medical image than the third medical image has to the first medical image; and a computing unit configured to run the trained function the computing unit further being configured to:

input the first, second and third medical images into the trained function;

determine a first degree of similarity between the first medical image and the second medical image and a second degree of similarity between the first medical image and the third medical image;

adjust the trained function such that first degree of similarity is greater than the second degree of similarity; and provide the adjusted trained function.

24. Computer-implemented method for identifying corresponding slices of medical image data sets (MIDS-1, MIDS-2), the method comprising the following steps:

receiving (S100, S100') a first medical image data set (MIDS-1);

receiving (S110) a second medical image data set (MIDS-2) different from the first medical image data set (MIDS-1);

identifying (S120, S120'), from a plurality of slices (S-2) comprised in the second medical image data set (MIDS-2), at least one corresponding slice based on degrees of similarity between the image data comprised in the first medical image data set (MIDS-1) and individual slices of the second medical image data set (MIDS-2).

25. Method according to point 24, wherein the first medical image data set (MIDS-1) comprises a plurality of slices (S-1); and the step of identifying the at least one corresponding slice comprises:

identifying (S120') for each of a plurality of slices (S-1) of the first medical image data set (MIDS-1) one corresponding slice of the second medical image data set (MIDS-2) so as to determine a slice correspondence (CS) between the first and second medical image data sets (MIDS-1, MIDS-2), with the degrees of similarity being respectively based on a similarity between an individual slice (S-1) of the first medical image data set (MIDS-1) and an individual slice (S-2) of the second medical image data set (MIDS-2).

26. Method according to point 25, further with the steps:
   determining (S320) an anatomical overlap between the image volume of first medical image data set (MIDS-1) and the image volume of the respective second medical image data set (MIDS-2) based on the identified slice correspondence (CS);
   evaluating (S330) a degree of comparability of the second medical image data set (MIDS-2) with the first medical image data set (MIDS-1) based on the determined anatomical overlap;
   providing the degree of comparability to a user via a user interface.

27 Method according to points 25 or 26, further with the steps of
   receiving (S210) an input from a user indicative of a selection of a slice of the first medical image data set (MIDS-1) in order to designate a selected slice;
   identifying (S220), from the plurality of slices (S-2) of the second medical image data set (MIDS-2), the slice corresponding to the selected slice based on the identified slice correspondence (CS); and
   providing the slice corresponding to the selected slice.

28. Method according to any of points 25 to 27, wherein in the step of identifying (S120') the at least one corresponding slice one or more of the following constraints are additionally being used:
   an overall degree of similarity is maximized, the overall degree of similarity being a measure for the cumulative similarity of individual slice pairs of first and second medical image data sets; and/or
   slice order of first and/or second medical image data sets is retained.

29. Method according to any of points 24-28, further with the steps:
   extracting an image descriptor from image data of the first medical image data set;
   respectively extracting a corresponding image descriptor from each of a plurality of slices of the second medical image data set;
   wherein the degrees of similarity are respectively based on a comparison between the extracted image descriptors of first and second medical image data sets.

30. Method according to point 29, wherein the first medical image data set comprises a plurality of slices and the method further comprises the step of:
   extracting an image descriptor from each of a plurality of slices of the first medical image data set.

31 Method according to any of points 24-30, wherein
   the first and second medical image data sets at least partially depict the same body part either
   of the same patient at different points in time, or
   of different patients.

32. Method according to any of points 24-31, wherein:
   first and second medical image data sets respectively comprise magnetic resonance image data;
   the first medical image data set has been acquired using a first magnetic resonance imaging protocol; and
   the second medical image data set has been acquired using a second magnetic resonance imaging protocol different to the first magnetic resonance imaging protocol.

33. Method according to any of points 24-32, wherein:
   the first medical image data set has been acquired using a first medical imaging modality;
   the second medical image data set has been acquired using a second medical imaging modality; and the first medical imaging modality is based on an imaging technology different from the imaging technology the second modality is based on, the first modality being preferably based on an x-ray imaging technology and the second medical image data set being preferably based on a magnetic resonance imaging technology.

34. Method according to any of points 24-33, wherein:
   the first medical image data set comprises a two-dimensional key image indicative of at least one finding previously reported for a patient; and
   the second medical image data set comprises an image study the reference image has been extracted from upon reporting the at least one finding for the patient.

35. Method according to any of points 24-34, further comprising
   resampling the second medical data set based on the first medical image data set in order to define a plurality of slices in the second medical image data set.

36. Method according to any of points 24-35, wherein the step of identifying the at least one corresponding slice comprises
   applying a trained function on the first and second medical image data sets, the trained function being adapted to determine degrees of similarities between two-dimensional medical images.

37. Method according to point 36, wherein the trained function applies a learned metric to determine degrees of similarity between two-dimensional medical images, the trained function preferably comprising a deep metric learning network.

38. Method according to points 36 or 37, wherein the trained function comprises a Siamese network and/or a triplet network.

39. Method according to any of points 36 to 38, wherein the trained function has been trained using a triplet loss function or a contrasting loss function.

40. Method according to any of points 36 to 39 wherein the trained function is configured to determine degrees of similarities between two-dimensional medical images by:
   comparing a first candidate image to a reference image and comparing a second candidate image to the reference image, the reference image being extracted from one of the first and second medical image data sets and the first and second candidate images being extracted from the respective other one of the first and second medical image data set; and
   determining which one of the first and second candidate images has a higher degree of similarity to the reference image.

41. Computer-implemented method for identifying corresponding slices in medical image data sets, the method comprising the following steps:
   receiving a two-dimensional key image indicative of at least one finding previously reported for a patient;
   retrieving a first medical image data set corresponding to the reference image;
   identifying, from a plurality of slices of the first medical image data set, at least one corresponding slice with respect to the reference image based on degrees of similarity between the reference image and individual slices of the first medical image data set so as to provide a first assignment between the reference image and a corresponding slice in the first medical image data;

receiving a second medical image data set, the second
medical image data set at least partially depicting the
same body part of the patient as the first medical
image data set but having been acquired at a different
point in time than the first medical image data set;
identifying, for each of a plurality of slices of the first
medical image data set one corresponding slice of a
plurality of slices of the second medical image data
set, the degrees of similarity being respectively
based on a similarity between an individual slice of
the first medical image data set and an individual
slice of the second medical image data set so as to
provide a second assignment between slices of the
first medical image data set and slices of the second
medical image data set;
selecting at least one slice from the second medical
image data set based on the first assignment and on
the second assignment so as to provide a selected
slice, the selected slice having a certain degree of
similarity to the reference image.
42. Computer-implemented method for determining a
degree of comparability of medical image data sets;
receiving a first medical image data set;
receiving a plurality of second medical image data sets,
first and second medical image data sets having been
acquired from the same patient at different points in
time, respectively;
for each second medical image data set:
identifying those slices having a corresponding slice
in the first medical image data set as overlapping
slices by determining degrees of similarity
between individual slices of the first medical
image data set and the respective second medical
image data set, wherein each degree of similarity
is based on a similarity of an individual slice of the
first medical image data set and an individual slice
of the respective second medical image data set;
and
determining an anatomical overlap between the
image volume of first medical image data set and
the image volume of the respective second medi-
cal image data set based on the overlapping slices;
determining a degree of comparability for each of the
second medical image data sets with the first medical
image data set based on the determined anatomical
overlaps.
43. Computer-implemented method for providing a
trained function comprising the following steps:
receiving a trained function;
providing a first two-dimensional medical image, a
second two-dimensional medical image, and a third
two-dimensional medical image, wherein:
first second and third medical images have been
extracted from one or more medical image studies
respectively depicting image volumes of body
parts of patients; and
the second medical image has a greater similarity to
the first medical image than the third medical
image has to the first medical image;
inputting the first, second and third medical images into
the trained function;
determine a first degree of similarity between the first
medical image and the second medical image and a
second degree of similarity between the first medical
image and the third medical image;

adjusting the trained function such that first degree of
similarity is greater than the second degree of simi-
larity; and
providing the trained function.
44. System for identifying corresponding slices of medi-
cal image data sets, the system comprising:
an interface for receiving a first medical image data set
and a second medical image data set different from
the first medical image data set; and
a computing unit configured to:
identify, from a plurality of slices comprised in the
second medical image data set, at least one cor-
responding slice based on degrees of similarity
between the image data comprised in the first
medical image data set and individual slices of the
second medical image data set.
45. System for determining a degree of comparability of
medical image data sets, the system comprising:
an interface for receiving a first medical image data set
and a plurality of second medical image data set
different from the first medical image data set, first
and second medical image data sets having been
acquired from the same patient at different points in
time, respectively; and
a computing unit configured to:
for each second medical image data set:
identify those slices having a corresponding slice in
the first medical image data set as overlapping
slices by determining degrees of similarity
between individual slices of the first medical
image data set and the respective second medical
image data set, wherein each degree of similarity
is based on a similarity of an individual slice of the
first medical image data set and an individual slice
of the respective second medical image data set;
and
determine an anatomical overlap between the image
volume of first medical image data set and the
image volume of the respective second medical
image data set based on the overlapping slices;
determine a degree of comparability for each of the
second medical image data sets with the first medical
image data set based on the determined anatomical
overlaps.
46. System for identifying corresponding slices in medi-
cal image data sets, the system comprising:
an interface for receiving a two-dimensional key image
indicative of at least one finding previously reported
for a patient, retrieving a first medical image data set
corresponding to the reference image, and a and a
second medical image data set, the second medical
image data set at least partially depicting the same
body part of the patient as the first medical image
data set but having been acquired at a different point
in time than the first medical image data set; and
a computing unit configured to:
retrieve the first medical image data set based on the
reference image via the interface;
identifying, from a plurality of slices of the first
medical image data set, at least one corresponding
slice with respect to the reference image based on
degrees of similarity between the reference image
and individual slices of the first medical image
data set so as to provide a first assignment between
the reference image and a corresponding slice in
the first medical image data;

identify, for each of a plurality of slices of the first medical image data set, one corresponding slice of a plurality of slices of the second medical image data set by evaluating similarities between the first and second medical image data sets using the trained function so as to provide a second assignment between slices of the first medical image data set and slices of the second medical image data set;

select at least one slice from the second medical image data set based on the first assignment and on the second assignment so as to provide a selected slice, the selected slice having a certain degree of similarity to the key image.

47. System for providing a trained function configured to determine a similarity between two-dimensional medical images, the system comprising:

an interface for receiving a trained function, a first two-dimensional medical image, a second two-dimensional medical image, and a third two-dimensional medical image, wherein:

first second and third medical images have been extracted from one or more medical image studies respectively depicting image volumes of body parts of patients; and the second medical image has a greater similarity to the first medical image than the third medical image has to the first medical image; and a computing unit configured to run the trained function the computing unit further being configured to:

input the first, second and third medical images into the trained function;

determine a first degree of similarity between the first medical image and the second medical image and a second degree of similarity between the first medical image and the third medical image;

adjust the trained function such that first degree of similarity is greater than the second degree of similarity; and provide the adjusted trained function.

The invention claimed is:

1. A computer-implemented method comprising:
receiving a first medical image data set;
extracting at least one image descriptor from image data of the first medical image data set, the at least one image descriptor from the image data of the first medical image data set being a first feature vector;
receiving a second medical image data set, the second medical image data set including a plurality of slices and being different from the first medical image data set;
extracting at least one image descriptor from each slice of the plurality of slices of the second medical image data set, the at least one image descriptor from each slice of the plurality of slices of the second medical image data set being a second feature vector;
comparing, with a trained function, the at least one image descriptor of the first medical image data set and the at least one image descriptor from each slice of the plurality of slices of the second medical image data set to generate a degree of similarity between the first medical image data set and each slice of the plurality of slices of the second medical image data set; and
identifying, from the plurality of slices of the second medical image data set, at least one corresponding slice based on the degrees of similarity between the first medical image data set and each slice of the plurality of slices of the second medical image data set, wherein
the trained function is configured to determine degrees of similarity between two-dimensional medical images, and
the trained function applies a learned metric to determine the degrees of similarity between the two-dimensional medical images, the trained function including a deep metric learning network.

2. The method according to claim 1, wherein
the first medical image data set comprises a plurality of slices, and
the identifying includes,
identifying, for each of the plurality of slices of the first medical image data set, one corresponding slice of the second medical image data set to determine a slice correspondence between the first medical image data set and the second medical image data set, the degrees of similarity being respectively based on a similarity between an individual slice of the first medical image data set and an individual slice of the second medical image data set.

3. The method according to claim 2, further comprising:
determining an anatomical overlap between an image volume of the first medical image data set and an image volume of the second medical image data set based on the identified slice correspondence;
evaluating a degree of comparability of the second medical image data set with the first medical image data set based on the determined anatomical overlap; and
providing the degree of comparability to a user via a user interface.

4. The method according to claim 2, further comprising:
receiving an input from a user indicative of a selection of a slice of the first medical image data set to designate a selected slice;
identifying, from the plurality of slices of the second medical image data set, a slice corresponding to the selected slice based on the identified slice correspondence; and
providing the slice corresponding to the selected slice.

5. The method according to claim 1, wherein the first medical image data set comprises a plurality of slices and the extracting the at least one image descriptor of the first medical data set includes
extracting an image descriptor from each of the plurality of slices of the first medical image data set.

6. The method according to claim 1, wherein:
the first medical image data set is associated with a first medical imaging modality,
the second medical image data set is associated with a second medical imaging modality, and
the first medical imaging modality is based on a first imaging technology different from a second imaging technology of the second medical imaging modality, the first imaging technology being an x-ray imaging technology and the second imaging technology being a magnetic resonance imaging technology.

7. The method according to claim 1, wherein:
the first medical image data set comprises a two-dimensional key image indicative of at least one finding previously reported for a patient; and
the second medical image data set comprises an image study a reference image has been extracted from upon reporting the at least one finding for the patient.

8. The method according to claim 1, further comprising:

resampling the second medical data set based on the first medical image data set in order to define the plurality of slices in the second medical image data set.

9. The method according to claim 1, wherein the trained function is configured to determine degrees of similarities between the two-dimensional medical images by:

comparing a first candidate image to a reference image and comparing a second candidate image to the reference image, the reference image being extracted from one of the first and second medical image data sets and the first and second candidate images being extracted from the respective other one of the first and second medical image data set; and determining which one of the first and second candidate images has a higher degree of similarity to the reference image.

10. A system comprising:

an interface configured to receive a first medical image data set and a second medical image data set, the second medical image data set including a plurality of slices and being different from the first medical image data set; and a computing unit configured to cause the system to, extract at least one image descriptor from image data of the first medical image data set, the at least one image descriptor from the image data of the first medical image data set being a first feature vector, extract at least one image descriptor from each slice of the plurality of slices of the second medical image data set, the at least one image descriptor from each slice of the plurality of slices of the second medical image data set being a second feature vector, compare, with a trained function, the at least one image descriptor of the first medical image data set and the at least one image descriptor from each slice of the plurality of slices of the second medical image data set to generate a degree of similarity between the first medical image data set and each slice of the plurality of slices of the second medical image data set, and identify, from the plurality of slices of the second medical image data set, at least one corresponding slice based on the degrees of similarity between the first medical image data set and each slice of the plurality of slices of the second medical image data set, wherein the trained function is configured to determine degrees of similarity between two-dimensional medical images, and the trained function applies a learned metric to determine the degrees of similarity between the two-dimensional medical images, the trained function including a deep metric learning network.

11. The system according to claim 10, wherein the first medical image data set comprises a plurality of slices, and the computing unit is configured to cause the system to, identify, for each of the plurality of slices of the first medical image data set, one corresponding slice of the second medical image data set to determine a slice correspondence between the first medical image data set and the second medical image data set, the degrees of similarity being respectively based on a similarity between an individual slice of the first medical image data set and an individual slice of the second medical image data set.

12. The system according to claim 11, wherein the computing unit is configured to cause the system to, determine an anatomical overlap between an image volume of the first medical image data set and an image volume of the second medical image data set based on the identified slice correspondence;

evaluate a degree of comparability of the second medical image data set with the first medical image data set based on the determined anatomical overlap; and provide the degree of comparability to a user via a user interface.

13. The system according to claim 11, wherein the computing unit is configured to cause the system to, receive an input from a user indicative of a selection of a slice of the first medical image data set to designate a selected slice;

identify, from the plurality of slices of the second medical image data set, the slice corresponding to the selected slice based on the identified slice correspondence; and provide the slice corresponding to the selected slice.

14. The system according to claim 10, wherein the first medical image data set comprises a plurality of slices and the extracting the at least one image descriptor of the first medical data set includes extracting an image descriptor from each of the plurality of slices of the first medical image data set.

15. A non-transitory computer-readable medium comprising program elements, when executed by a computing unit, are configured to cause the method of claim 1 to be performed.

\* \* \* \* \*